United States Patent [19]

Juji et al.

[11] Patent Number: 5,098,371
[45] Date of Patent: Mar. 24, 1992

[54] SWITCH BAG TYPE BLOOD GATHERING SET

[75] Inventors: Takeo Juji, Matsudo; Nobuhiro Wakimoto; Yoichi Kagawa, both of Tokyo; Seiichi Ono, Ohita, all of Japan

[73] Assignee: Kawasumi Laboratories, Inc., Tokyo, Japan

[21] Appl. No.: 262,295

[22] Filed: Oct. 24, 1988

[30] Foreign Application Priority Data

Oct. 24, 1987 [JP] Japan .................. 62-267640
Oct. 24, 1987 [JP] Japan .................. 62-267641
Oct. 24, 1987 [JP] Japan .................. 62-267642

[51] Int. Cl.$^5$ .................................. A61M 37/00
[52] U.S. Cl. .................................. 604/4; 604/6; 604/410
[58] Field of Search ............. 604/4, 5, 6, 403, 405, 604/408, 410, 411

[56] References Cited

U.S. PATENT DOCUMENTS

| | | | |
|---|---|---|---|
| 3,655,123 | 4/1972 | Judson et al. | 604/6 X |
| 3,945,380 | 3/1976 | Dabney et al. | 604/410 |
| 4,282,863 | 8/1981 | Beigler et al. | 604/410 X |
| 4,428,745 | 1/1984 | Williams | 604/6 |
| 4,786,286 | 11/1988 | Cerny et al. | 604/406 |
| 4,846,995 | 7/1989 | Minagawa | 604/410 |
| 4,850,995 | 7/1989 | Tie et al. | 604/6 |

Primary Examiner—Mickey Yu
Assistant Examiner—Kerry Owens
Attorney, Agent, or Firm—Michael J. Striker

[57] ABSTRACT

This invention is a switch bag type blood-gathering set used for transfusing blood gathered from a blood donor to the same blood donor again, and for newly gathering predetermined amount of blood from the blood donor. This switch bag type blood-gathering set comprises a liquid transferring member for introducing a physiological saline solution into the blood-gathering set, a blood transfusing member for introducing blood from a blood bag into the blood-gathering set, a blood-transfusing and gathering member for supplying blood to or gathering blood from the donor, a washing solution storing member for containing a waste liquor after priming in the blood-gathering set, and a blood storing member for storing blood gathered from the donor, and these constituents are connected by connecting tubes so as to not contact with the air outside.

6 Claims, 20 Drawing Sheets

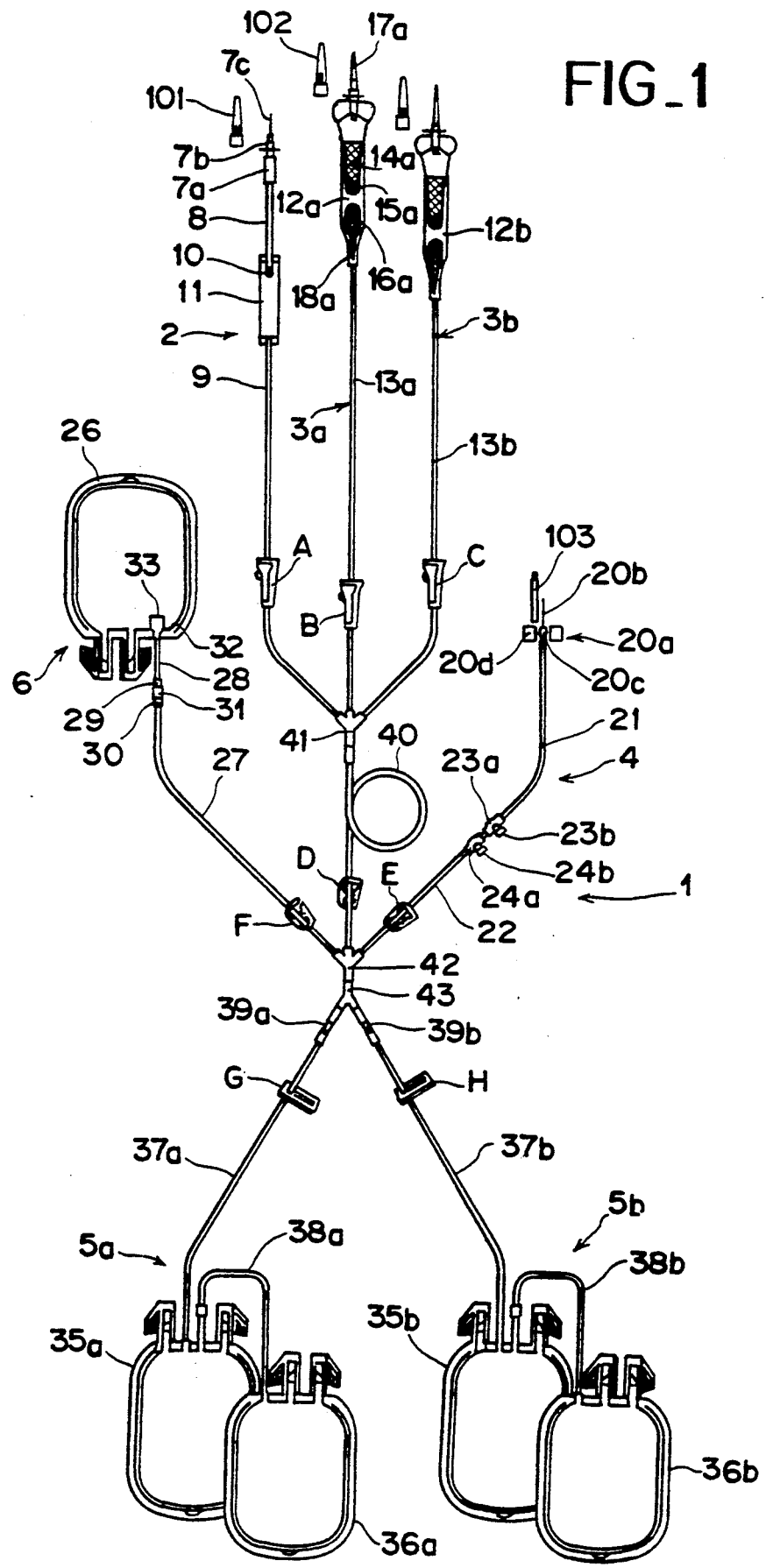
FIG_1

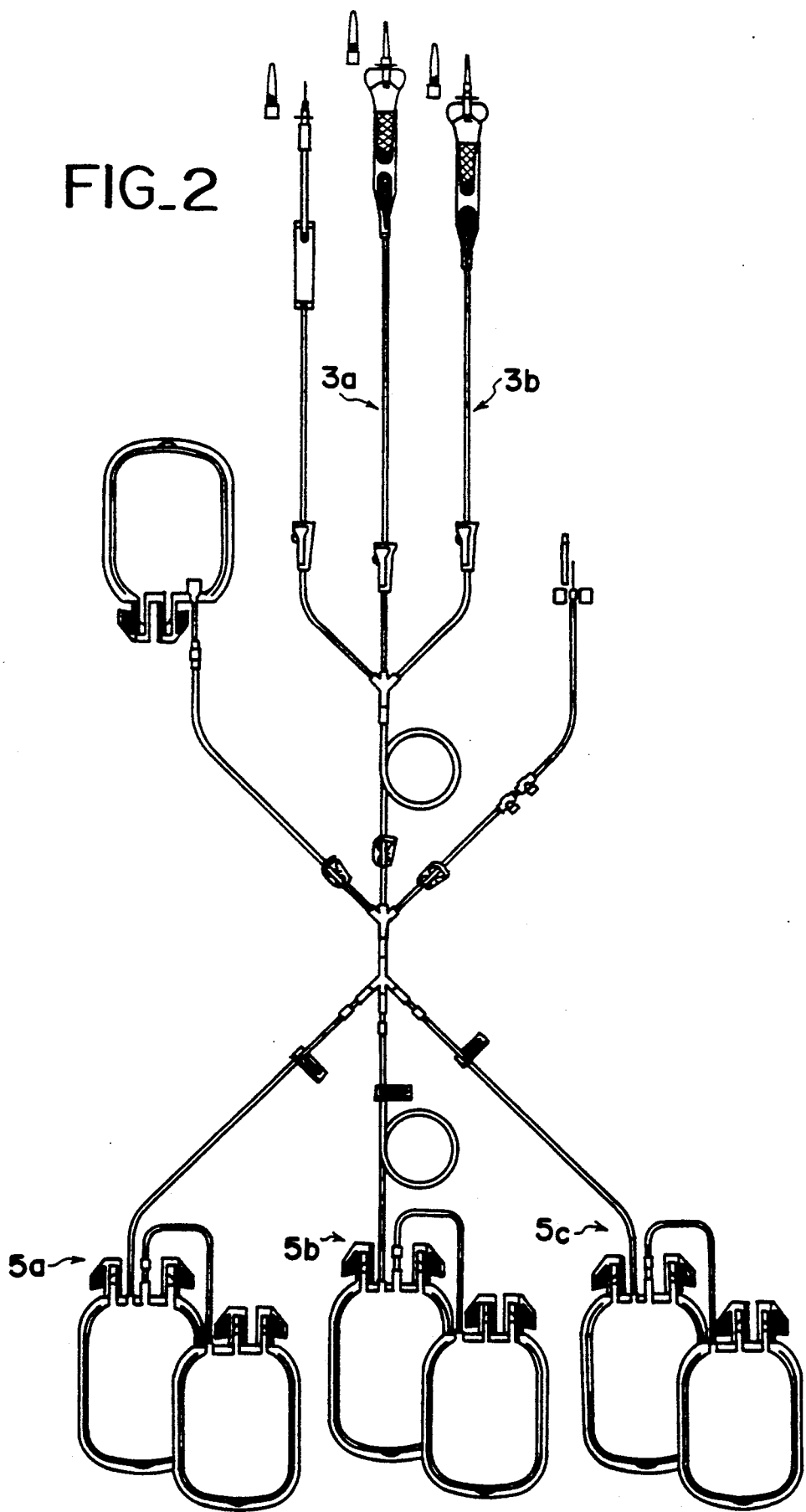
FIG_2

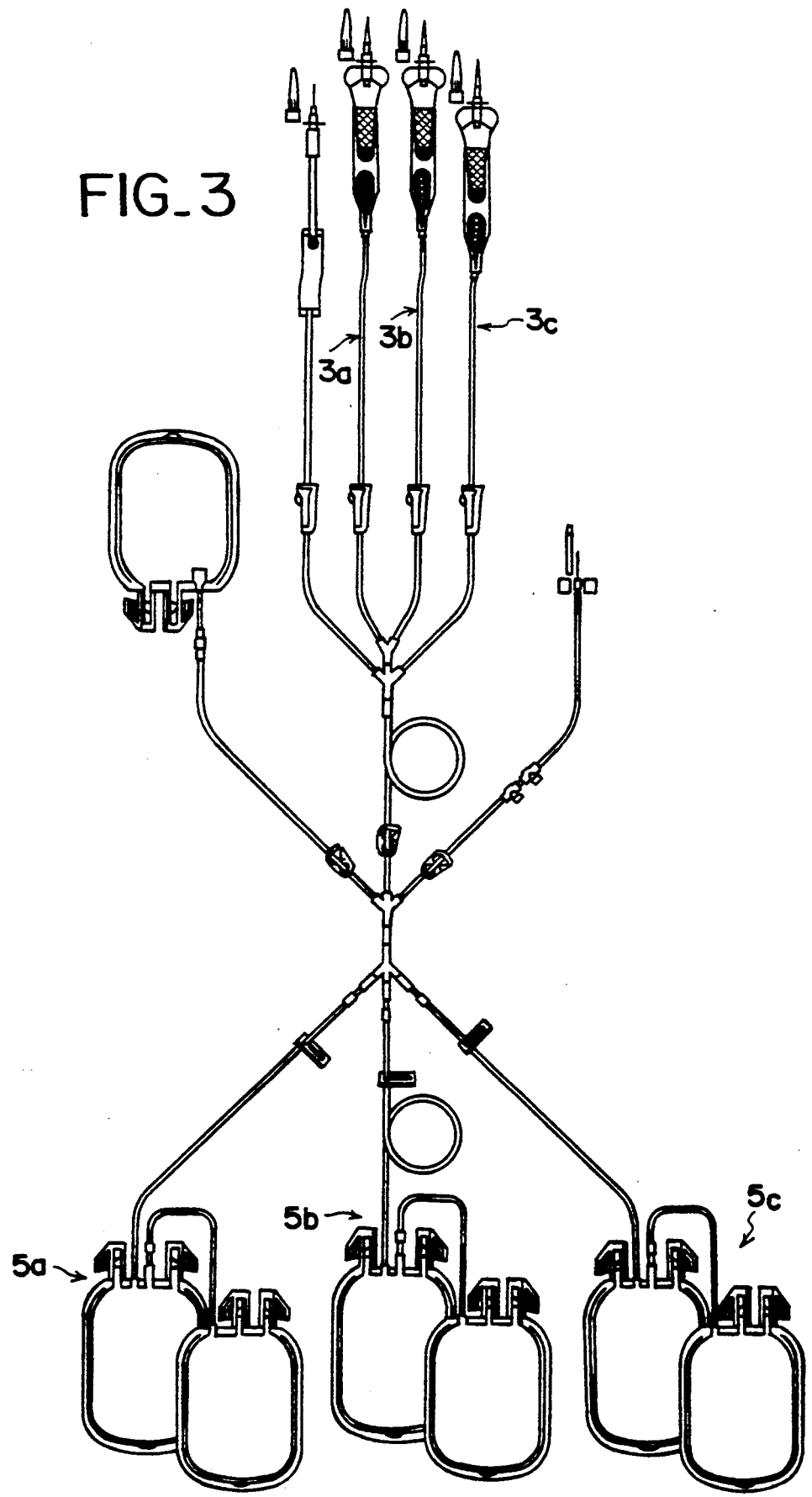
FIG_3

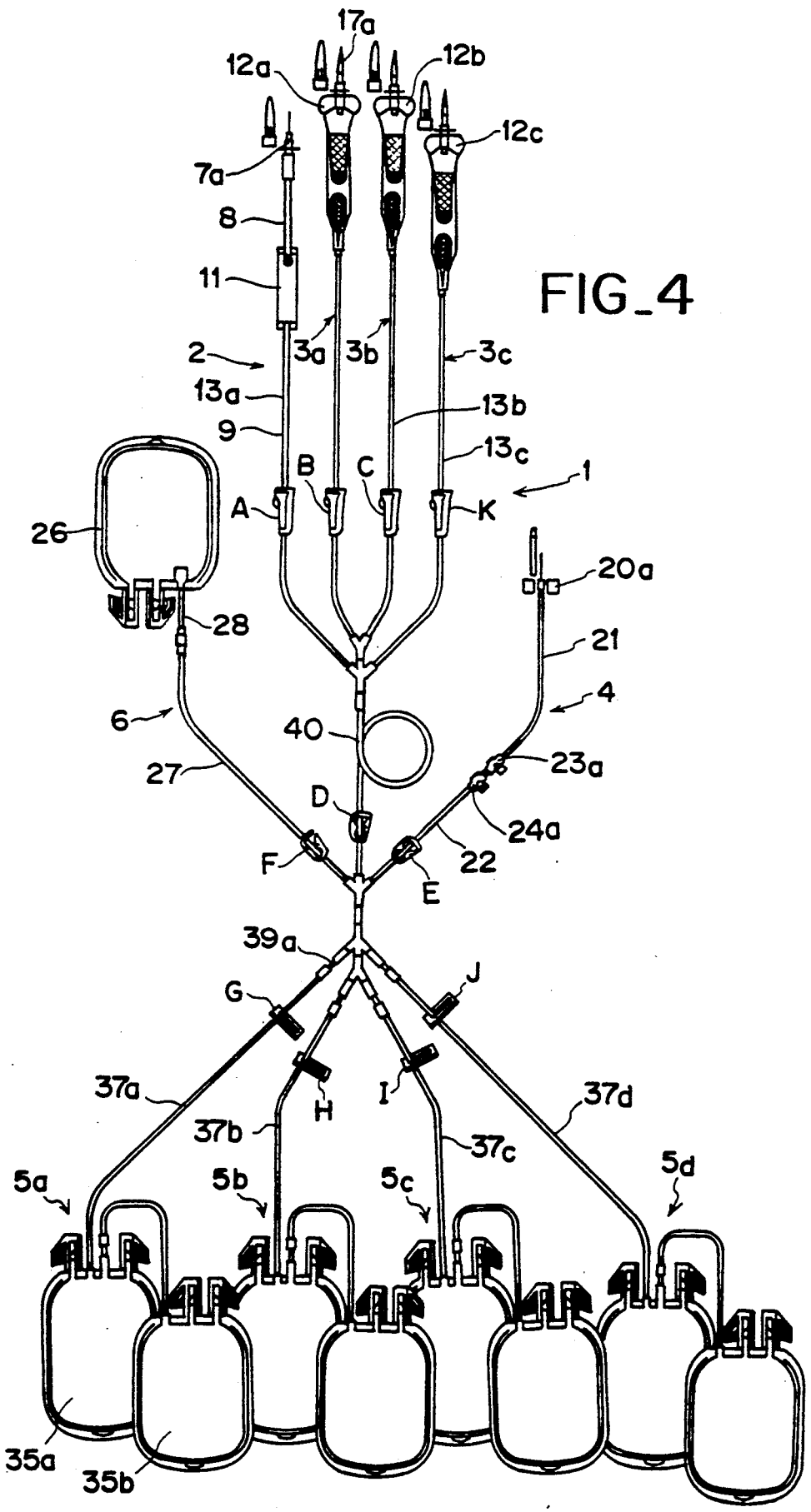
FIG_4

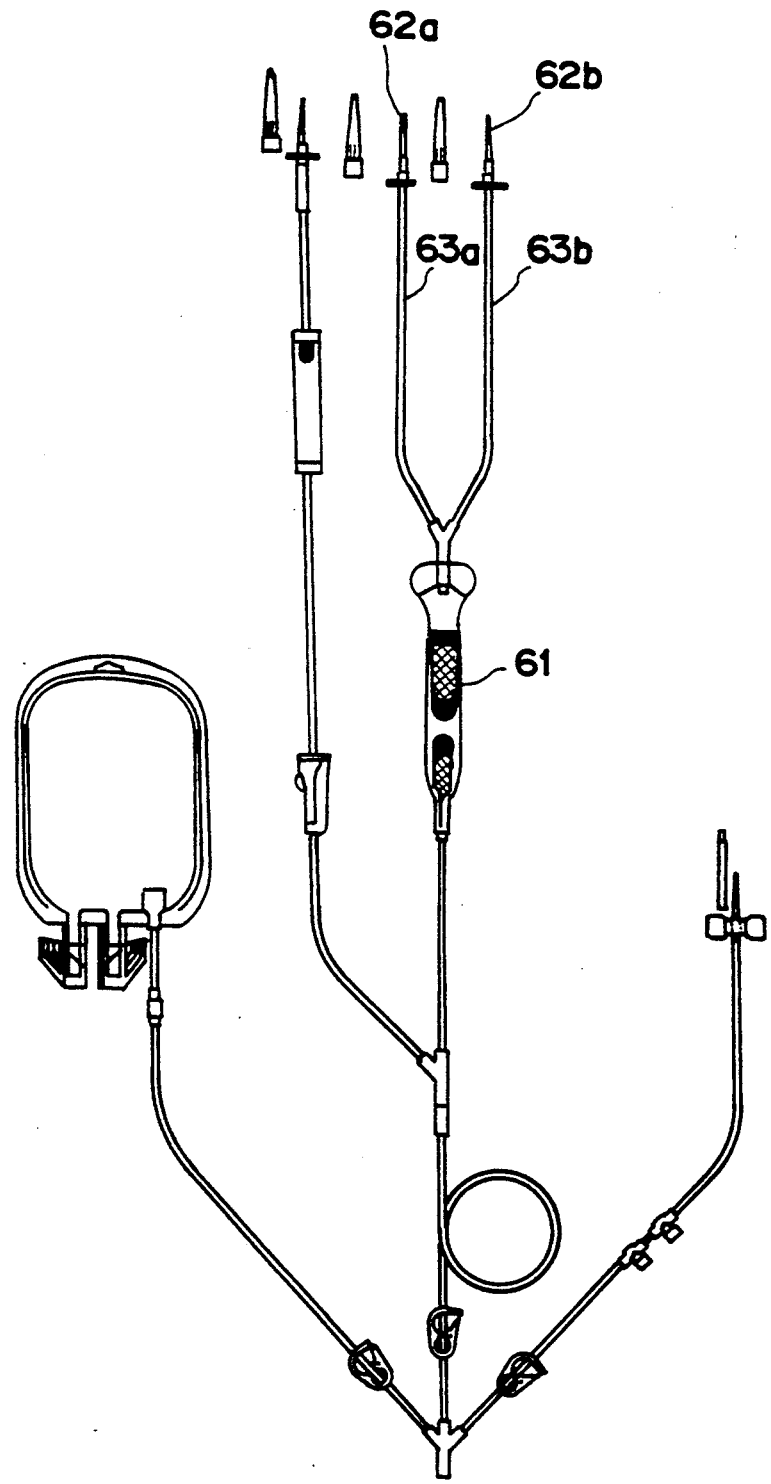
FIG_5(a)

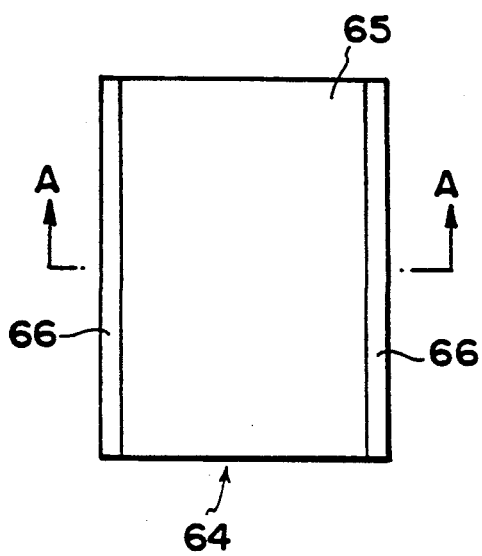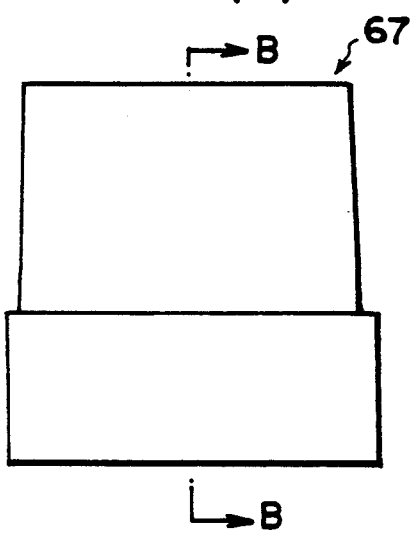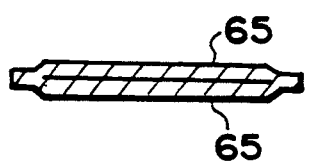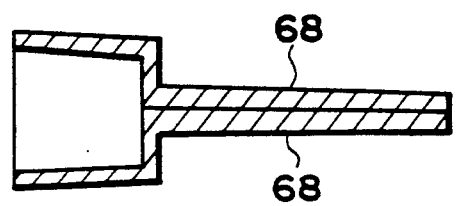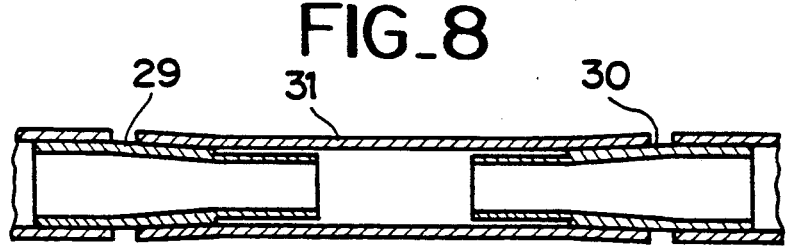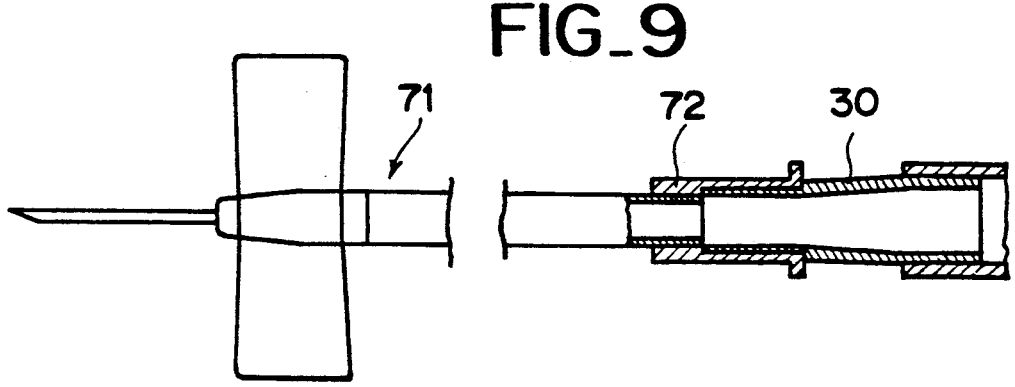

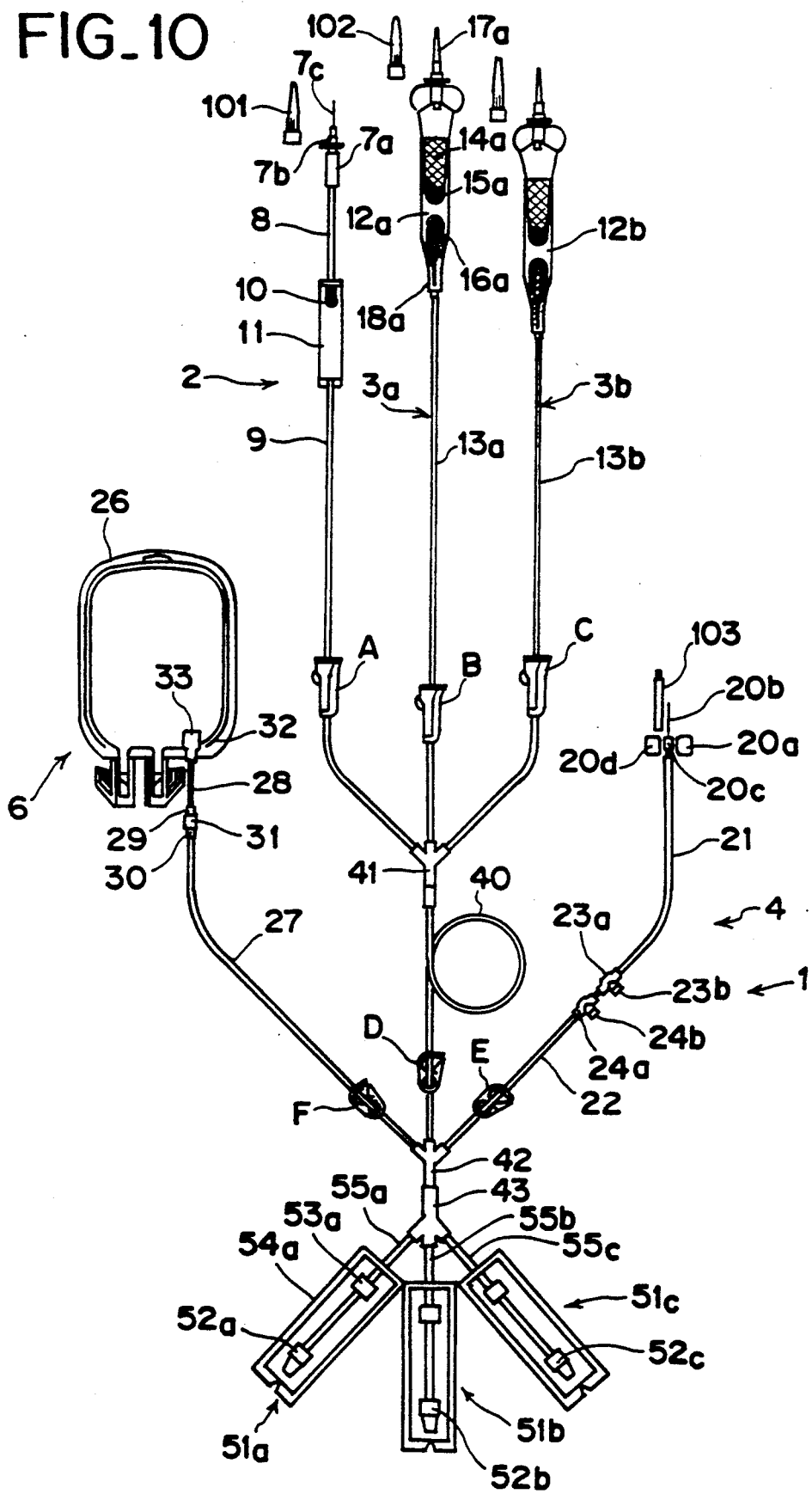

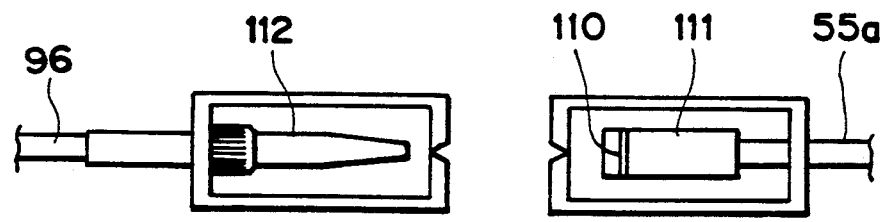
FIG._13
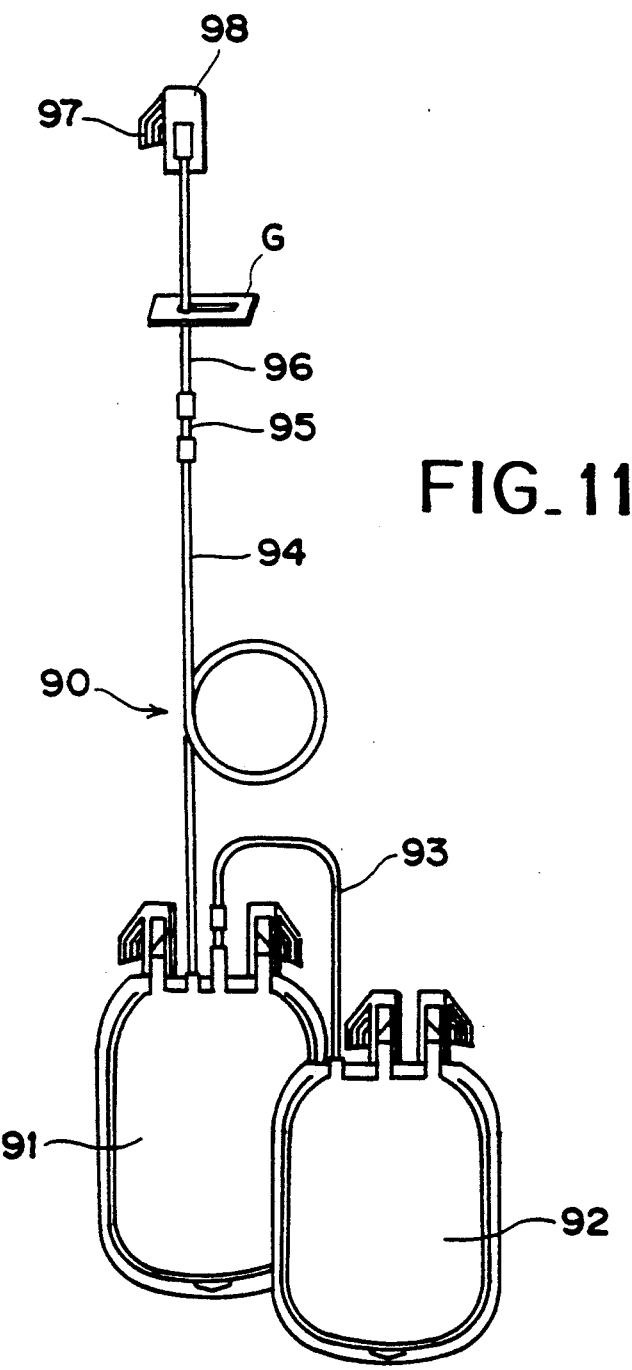
FIG._11

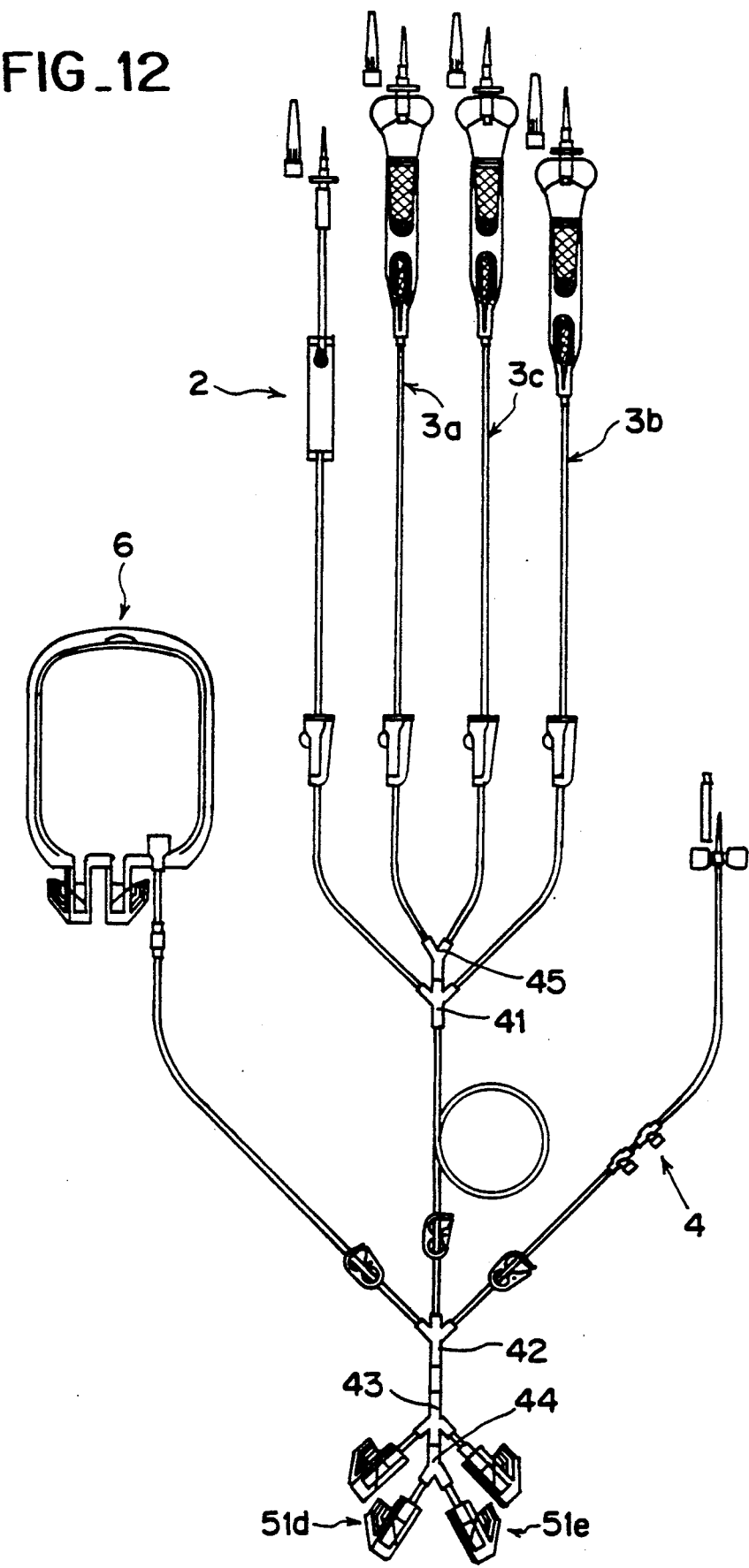
FIG_12

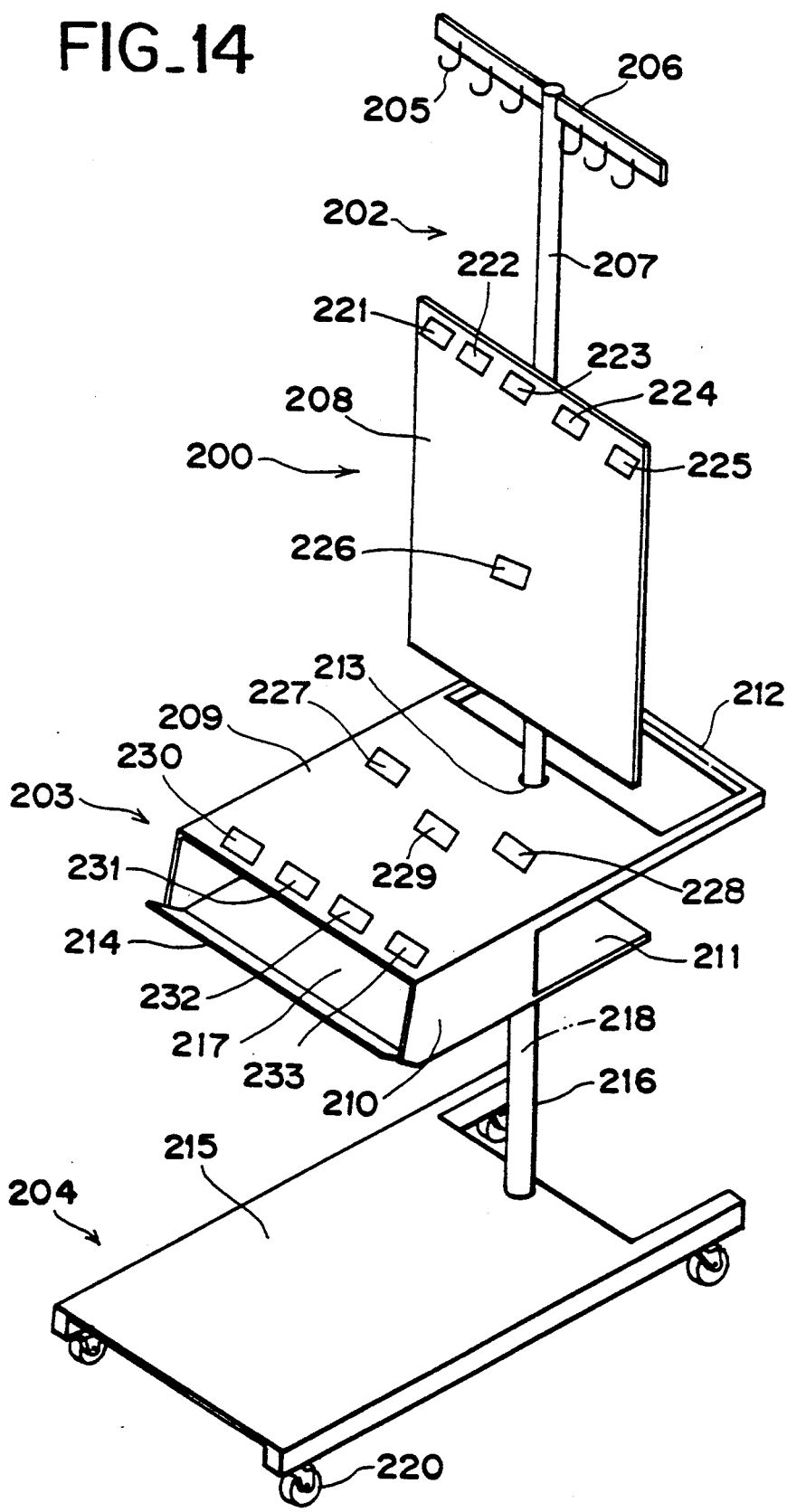
FIG_14

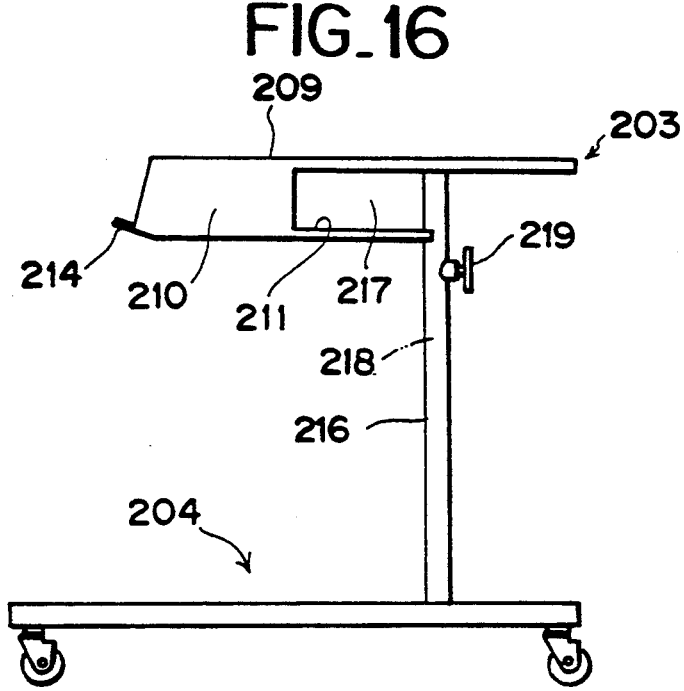
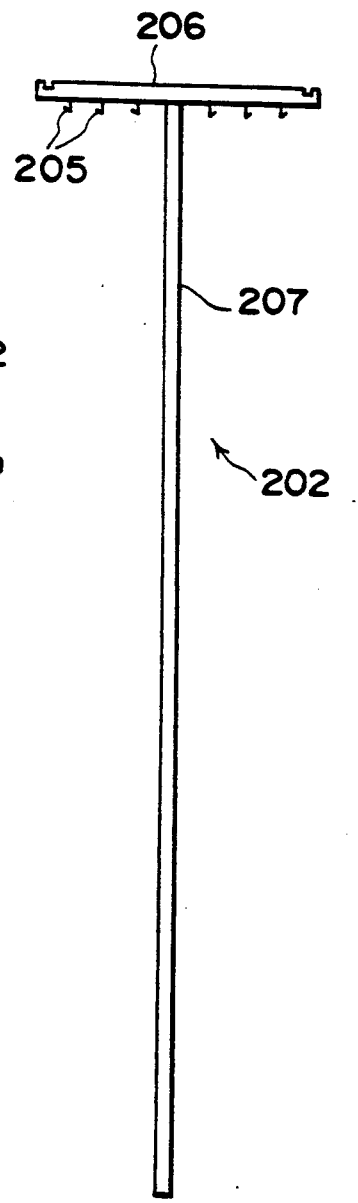
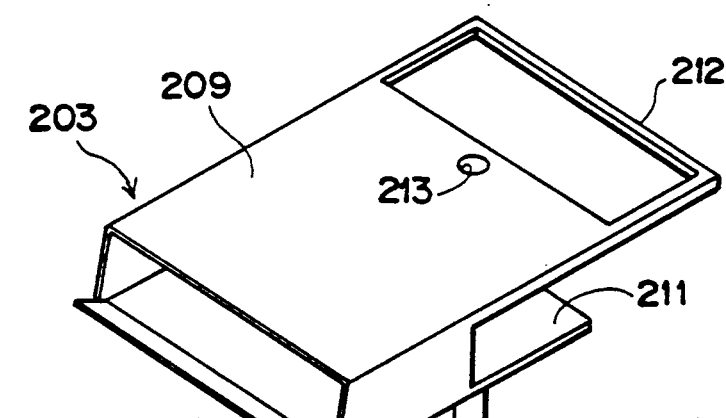

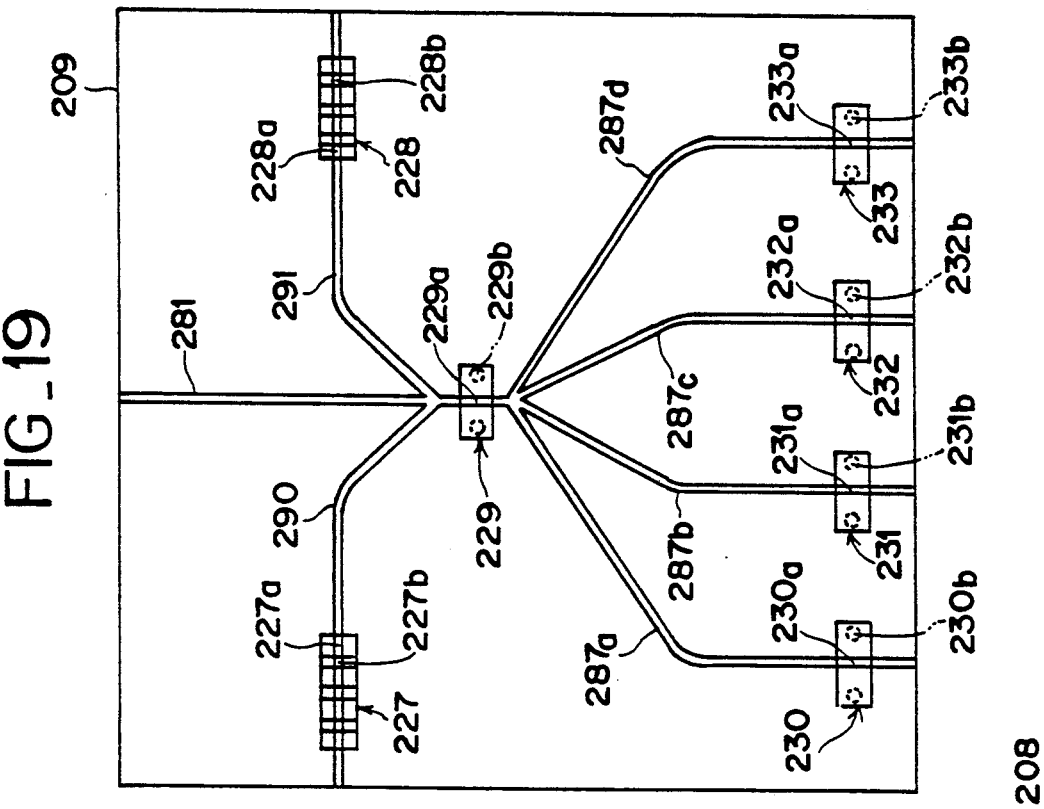
FIG_19
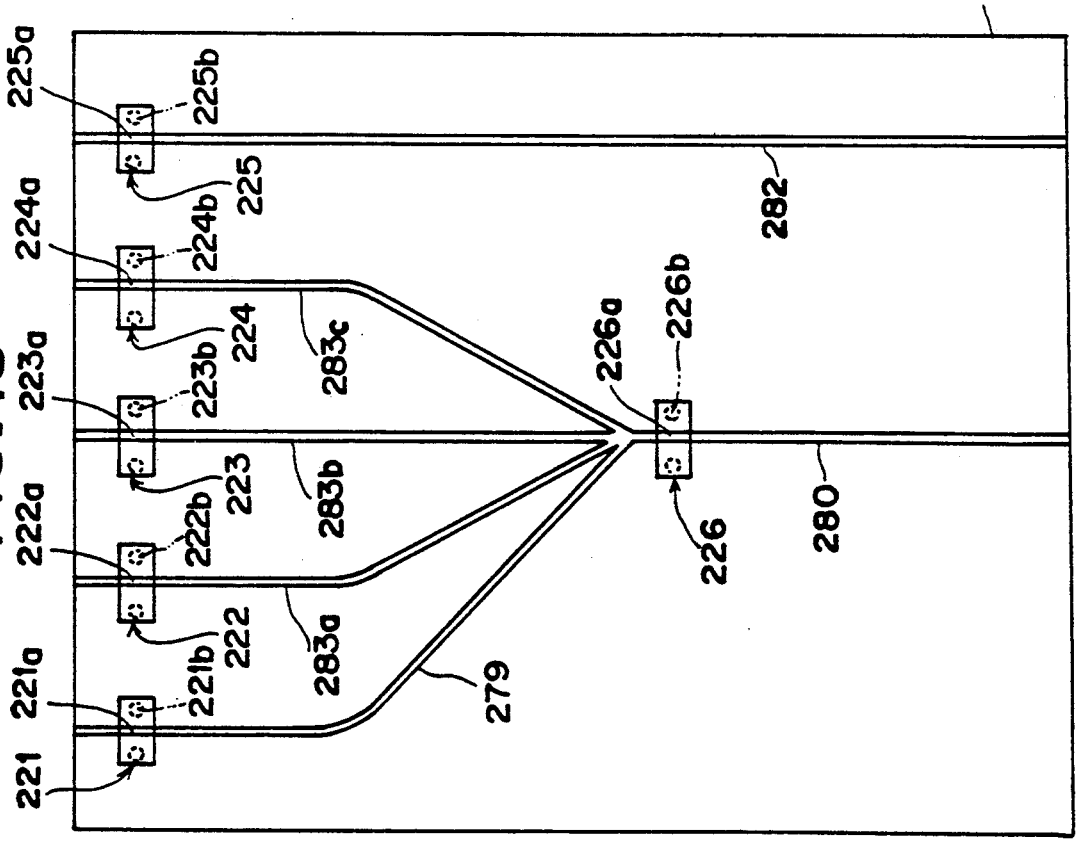
FIG_18

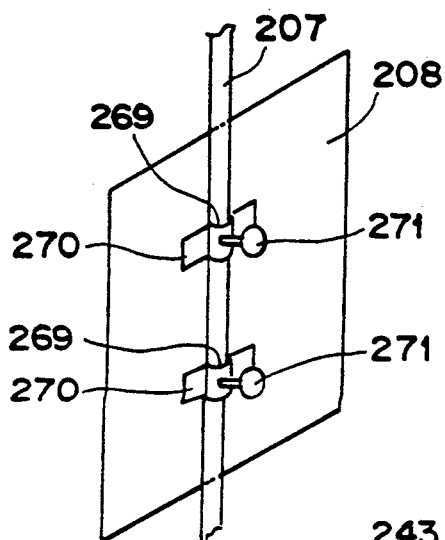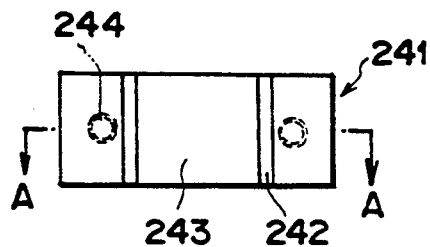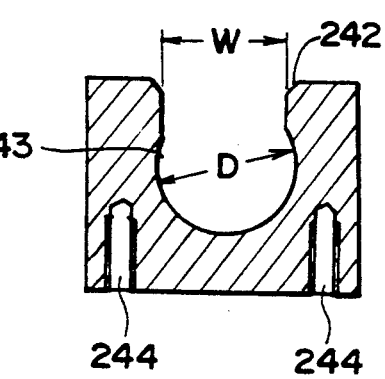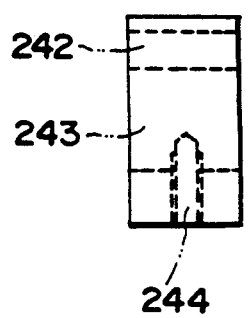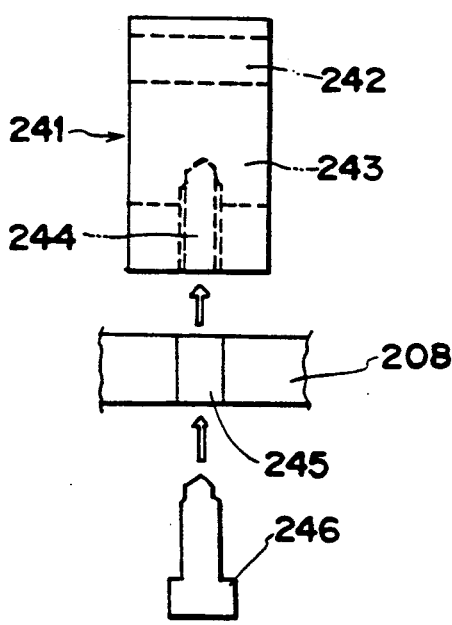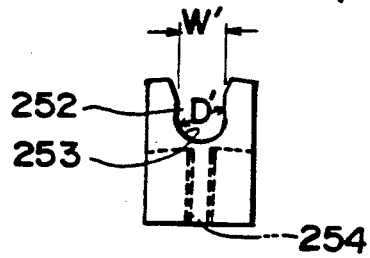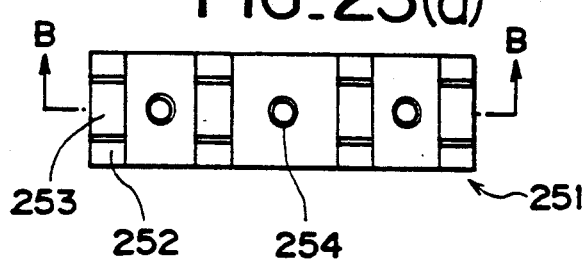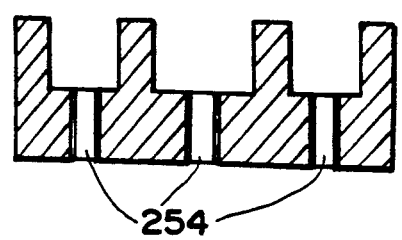

FIG_24
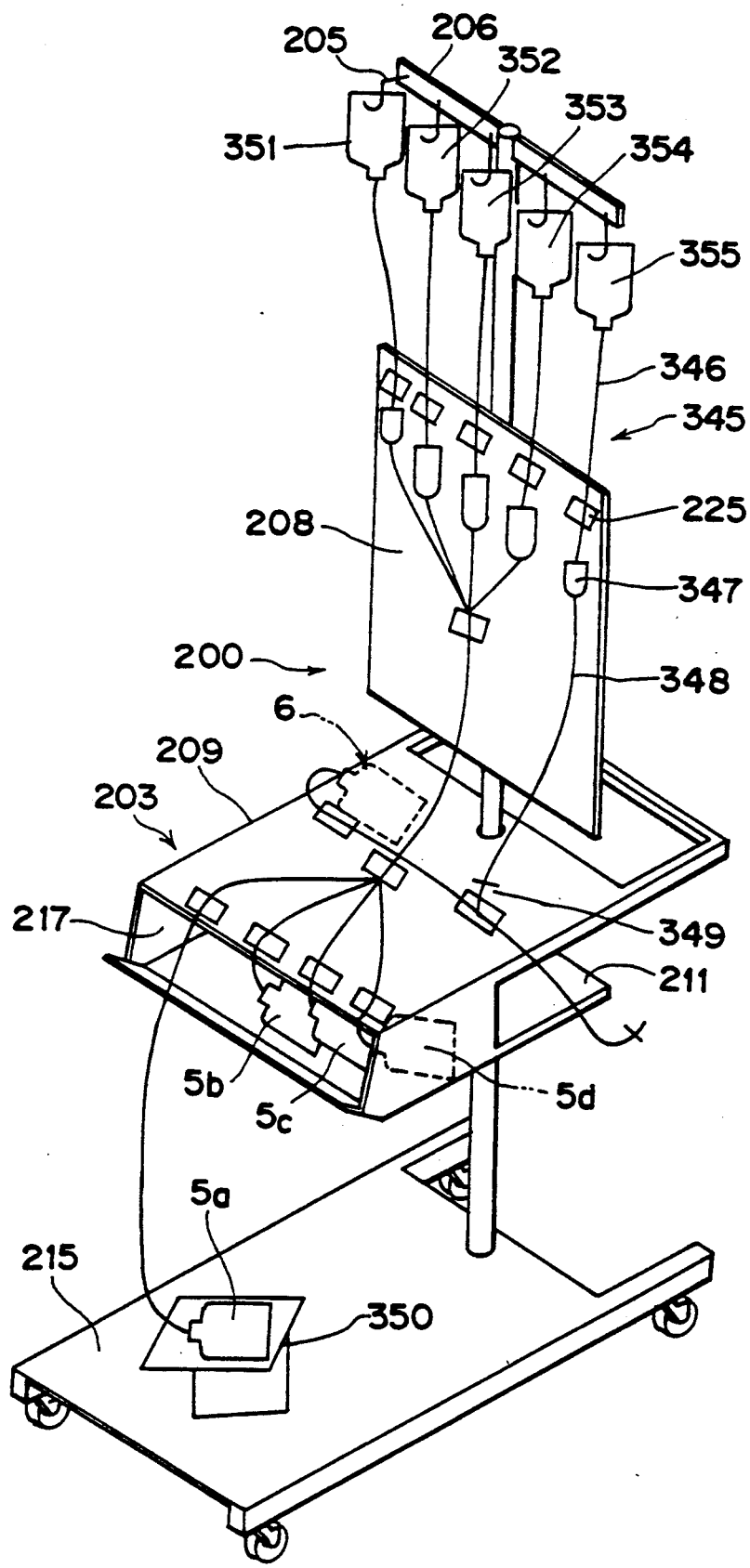

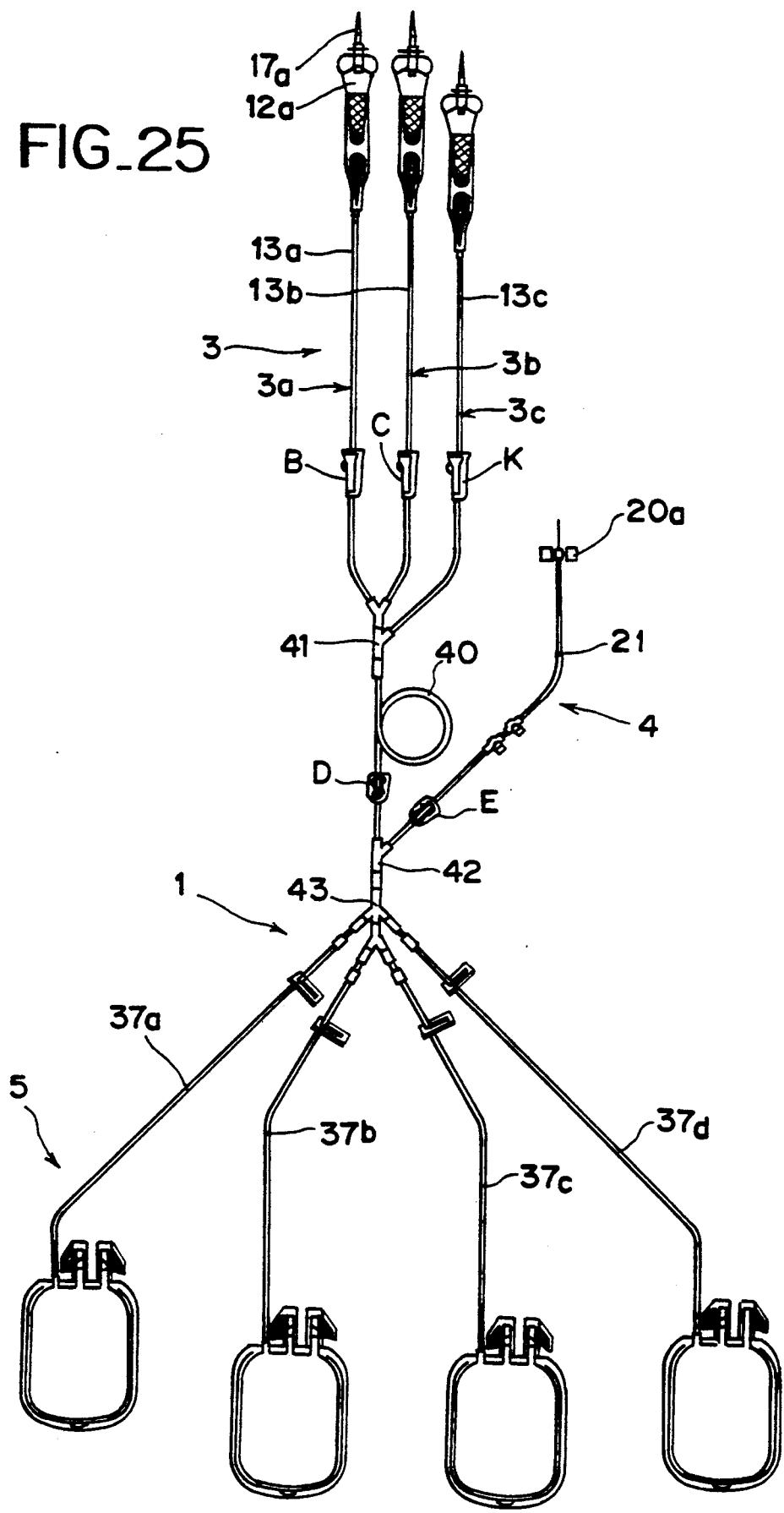

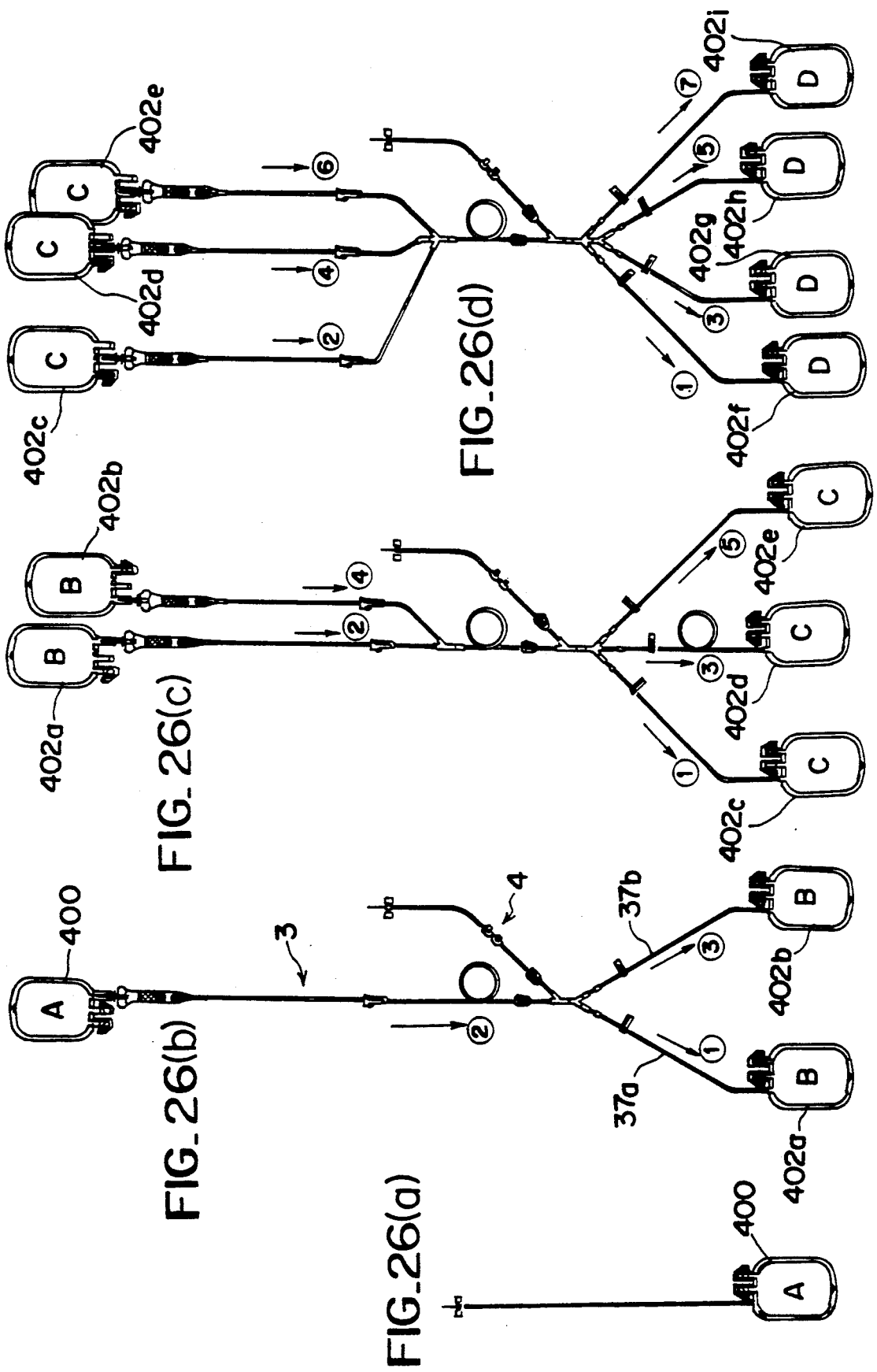

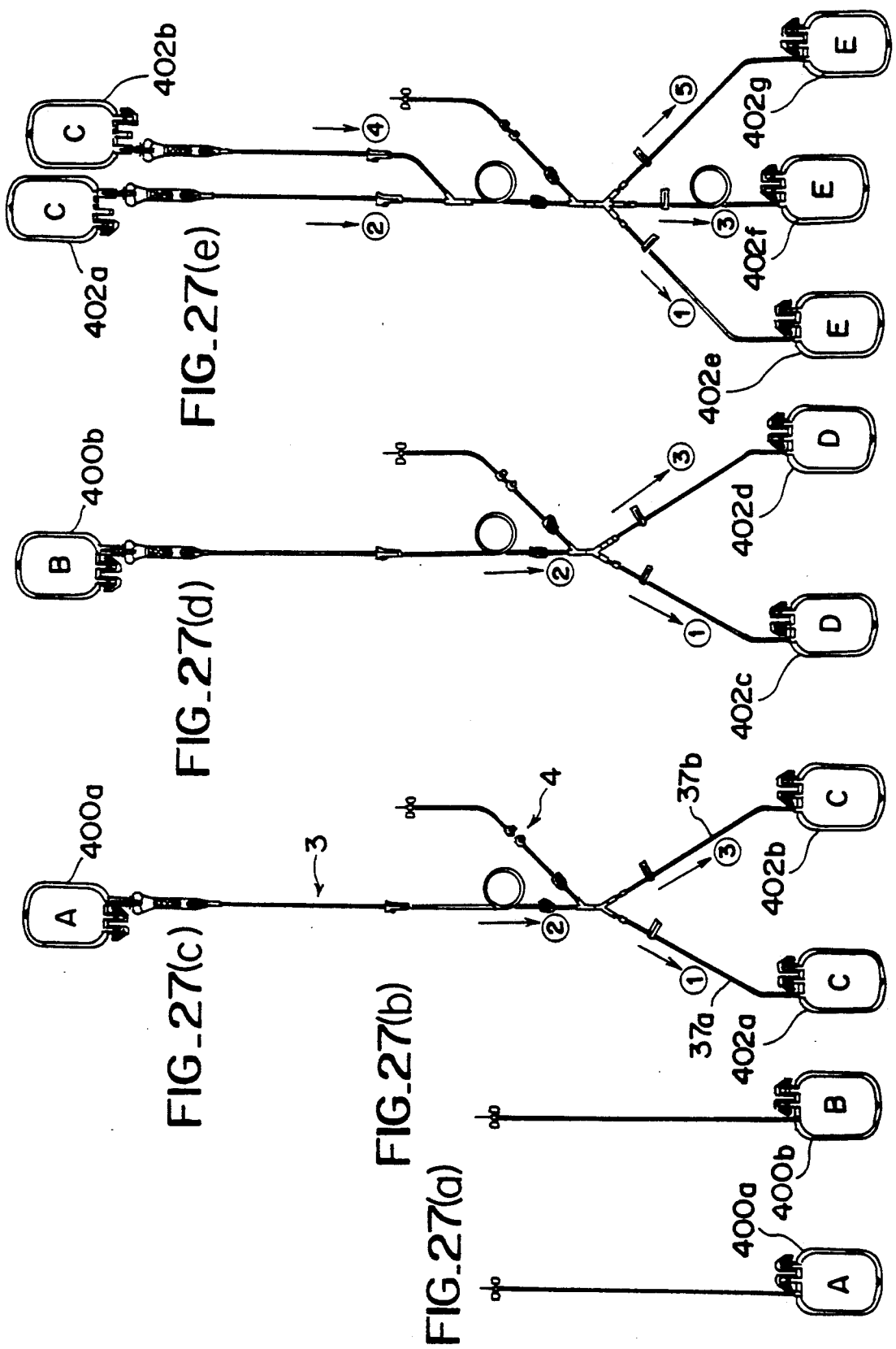

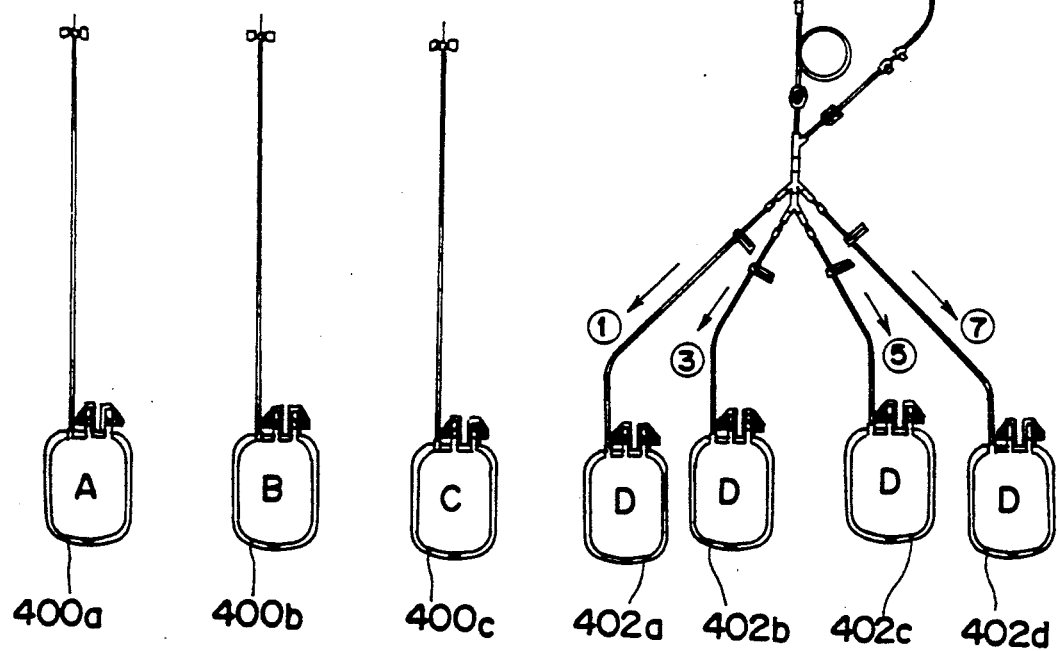

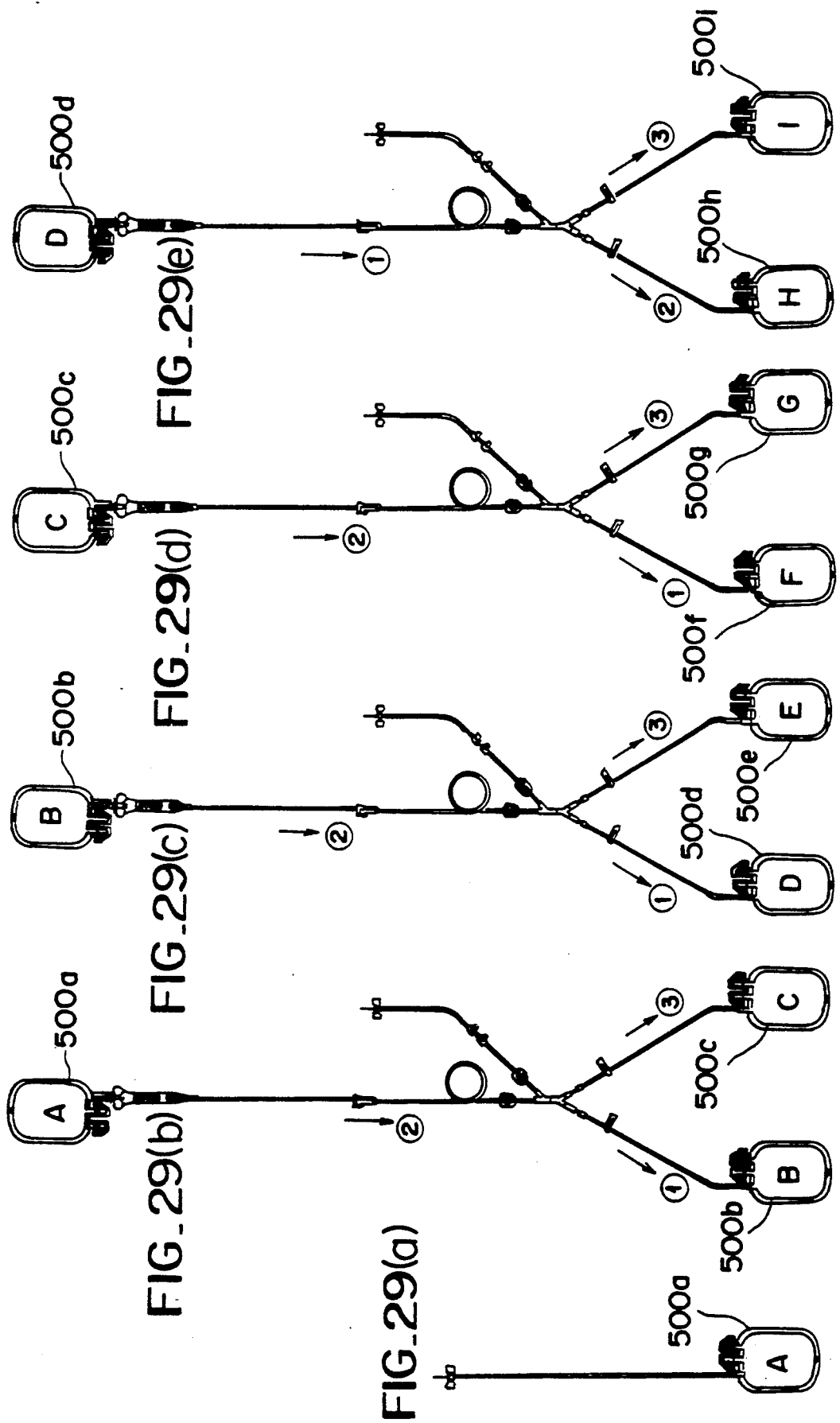

SWITCH BAG TYPE BLOOD GATHERING SET

BACKGROUND OF THE INVENTION

This invention relates to a switch bag type blood-gathering set to effect blood transfusion of stored blood and blood-gathering of fresh blood at the same time, an operating panel apparatus of the blood-gathering set and a blood-gathering method using the blood-gathering set.

Blood gathered in a plastic bag should be used within 21 days, but, actually, it has been used within 7 days or so in many cases.

When the gathered blood is stored for a long time, hemolysis or formation of microaggregates in blood proceeds. It is preferred not to use such a blood for transfusion and, therefore the gathered blood should desirably be employed for transfusion as soon as possible.

Also, an amount of blood gathered from a blood donor at one time is limited to a range of 400 ml to 500 ml. This is because if a large amount of blood is gathered from a blood donor at once, effects to a living body, such as anemia, decrease in blood component, etc. are serious in view of balance of body fluids.

Further, fresh blood of other person includes a risk of infection with syphilis, hepatis, etc. so that it has been conducted to establish a method in which self-blood is transfused.

Particularly, to the patient who can be conducted an expected operation in addition to articulatio coxae shelf rotatory born cutting operation, scoliosis operation and artificial articulatio coxae whole replacement operation, and who can be capable of gathering blood, it is preferred to employ a technique for predeposit of autologus blood in which autologus blood is gathered and reserved, and the the stored blood is transfused at the operation.

For this method, the technique for predeposit of autologus blood gathered before an operation such as the refrigerator storing method or the Leapfrog method (liquid state storing method) has heretofore been employed.

For example, an example of the Leapfrog method will be explained by referring to FIG. 29.

As the first time, one unit of a blood A is gathered in a blood storing bag 500a (see FIG. 29(a)), and at the second time, as shown in FIG. 29(b),
(1) one unit of a blood B is gathered from a patient into a blood storing bag 500b,
(2) a blood A in the blood storing bag 500a is transfused to the patient, and
(3) one unit of a blood C is again gathered from the patient into a blood storing bag 500c, whereby the blood B or the blood C in excess of one unit from that of the fist time is gathered.

As the third time (see FIG. 20(c)),
(1) one unit of a blood D is gathered from the patient,
(2) one unit of the blood B gathered at the second time is transfused to the patient, and
(3) one unit of a blood E is gathered from the patient.

At the fourth time (see FIG. 29(d)),
(1) one unit of a blood F is gathered,
(2) one unit of the blood C gathered at the second time is transfused to the patient, and
(3) one unit of a blood G is gathered from the patient.

At the fifth time (see FIG. 29(e)),
(1) one unit of a blood H is gathered,
(2) one unit of the blood D gathered at the third time is transfused to the patient, and
(3) one unit of a blood I is gathered from the patient.

Thus, one unit of the blood gathered at the previous time is returned and at the same time, two units of blood is gathered so that stored amounts of blood can be increased.

However, in the Leapfrog method, there are problems that (1) the stored amount of blood is limited, (2) oxygen transferability of the blood becomes low, and (3) blood-gathering term is limited, etc., and in the refregirator storing method, there are also problems in loss of blood cells at thawing, or in costs for storing and thawing.

SUMMARY OF THE INVENTION

The present invention relates to a switch bag type blood-gathering set used for transfusing blood, which is previously gathered from a blood donor and reserved, to said blood donor and for newly gathering blood from said blood donor, and is constituted by a liquid transferring member for introducing a liquid medicine such as a physiological saline solution into said blood-gathering set; a blood transfusing member for introducing blood in a blood bag into said blood-gathering set; a blood-transfusing and gathering member for transfusing the blood from said blood transfusing member to a blood donor or blood-gathering from a blood-transfusing and gathering needle; a washing solution storing member for recovering a waste liquor after priming in said blood-gathering set; and a blood storing member for storing the blood gathered from said blood-transfusing and gathering member. Thus, it can be provided a blood-gathering set which can transfuse blood without losing freshness of the blood gathered from a blood donor as well as can gather blood with an amount larger than that transfused to the blood donor without preventing balance of body fluid.

Also, an object of the present invention is to provide a blood-gathering set excellent in sanitation, which can effect a blood gathering operation from a blood donor and a blood transfusing operation to a blood receptor with a closed system by connecting the above members with connecting tubes closely so as to prevent invasion of the outside air.

Further, the present invention is to provide an operating panel apparatus convenient for blood-transfusing and gathering operation according to the above switch bag type blood-gathering set, comprising a stand member for hanging a blood bag and a liquid transferring bag, and separately fixing plural number of connecting tubes connected to these bags; a main body in which a blood storing bag, etc. are contained therein and plural number of connecting tubes which connect to the connecting tubes fixed to said stand member can be fixed separately to a ceiling board; a moving member in which wheels are attached thereto; and a height adjusting system of said stand member; whereby an operation panel apparatus which is convenient for operation of the above switch bag type blood-gathering set is provided.

Furthermore, the present invention is a technique for predeposit of autologus blood carried out by using a blood-gathering set composed of at least a blood transfusing member, a blood-transfusing and gathering member and a blood storing member, which comprises a step of transfusing blood of unit n gathered at the Nth time to a patient at the (N+1)th time and a step of newly gathering blood of unit (n+1) and reserving, and transfusing said blood to the patient at the (N+2)th time, whereby a blood-gathering method in which autologous blood can sufficiently be gathered before an operation required therefore and the blood can be stored with a state of good oxygen transferability, etc.

BRIEF DESCRIPTION OF THE DRAWINGS

FIG. 1 is a schematic view showing a basic constitution of the switch bag type blood-gathering set of the present invention;

FIG. 2, FIG. 3 and FIG. 4 are schematic views showing modified examples of the switch bag type blood-gathering set shown in FIG. 1;

FIG. 6 is an example of a check valve provided to a washing solution storing member wherein 6(a) is a plane view and 6(b) is a sectional view of A—A;

FIG. 7 is another example of the check valve as the same above wherein 7(a) is a plane view and 7(b) is a sectional view of B—B;

FIG. 8 is an enlarged view at the neighbour of a connecting tube of a washing solution storing member;

FIG. 9 is a schematic view for explaining a using example of male lure connector of a washing solution storing member;

FIG. 10 is a schematic view showing other example of a switch bag type blood-gathering set of the present invention;

FIG. 11 is a schematic view of a blood storing member in which the switch bag type blood-gathering set of FIG. 10 is used by connecting thereto;

FIG. 12 is a schematic view showing a modified example of the blood-gathering set of FIG. 10;

FIG. 13 is a schematic view showing other example of a connecting portion of a connecting member and a blood storing member of the switch bag type blood-gathering set of FIG. 10;

FIG. 14 is a schematic view of an operation panel of a switch bag type blood-gathering set of the present invention;

FIG. 15 is a perspective view of a body of the above operating panel and a moving member;

FIG. 16 is a side view of the operating panel of FIG. 15;

FIG. 17 is a schematic view of a stand member of an operating panel;

FIG. 18 is an enlarged view of a backboard of an irigator member;

FIG. 19 is an enlarged view of a ceiling board of a body;

FIG. 20 is a schematic view showing a fixed state of a prop of a stand member and a backboard;

FIG. 21 shows a fixing member to fix a connecting tube of a switch bag type blood-gathering set to a backboard of an operating panel and a ceiling board, wherein 21(a) is a plane view, 21(b) is a side view and 21(c) is a sectional view;

FIG. 22 is a schematic view for explaining a method to fix the above fixing member to a backboard (ceiling board) of an operating panel;

FIG. 23 is a schematic view showing other example of the fixing member of FIG. 21, wherein 23(a) is a plane view, 23(b) is a side view and 23(c) is a sectional view;

FIG. 24 is a schematic view in which a switch bag type blood-gathering set of the present invention is attached to an operating panel;

FIG. 25 is a schematic view of a switch bag type blood-gathering set to be used for a technique for predepodit of autologus blood storing method of the present invention;

FIGS. 26a-26d, FIG. 27a-27e and FIGS. 28a-28d are schematic views for explaining a technique for predeposit of autologus blood storing method of the present invention; and FIG. 29(a) to 29(e) are schematic views showing the conventional technique for predeposit of autologus blood.

DESCRIPTION OF THE PREFERRED EMBODIMENT

Figure 5B:
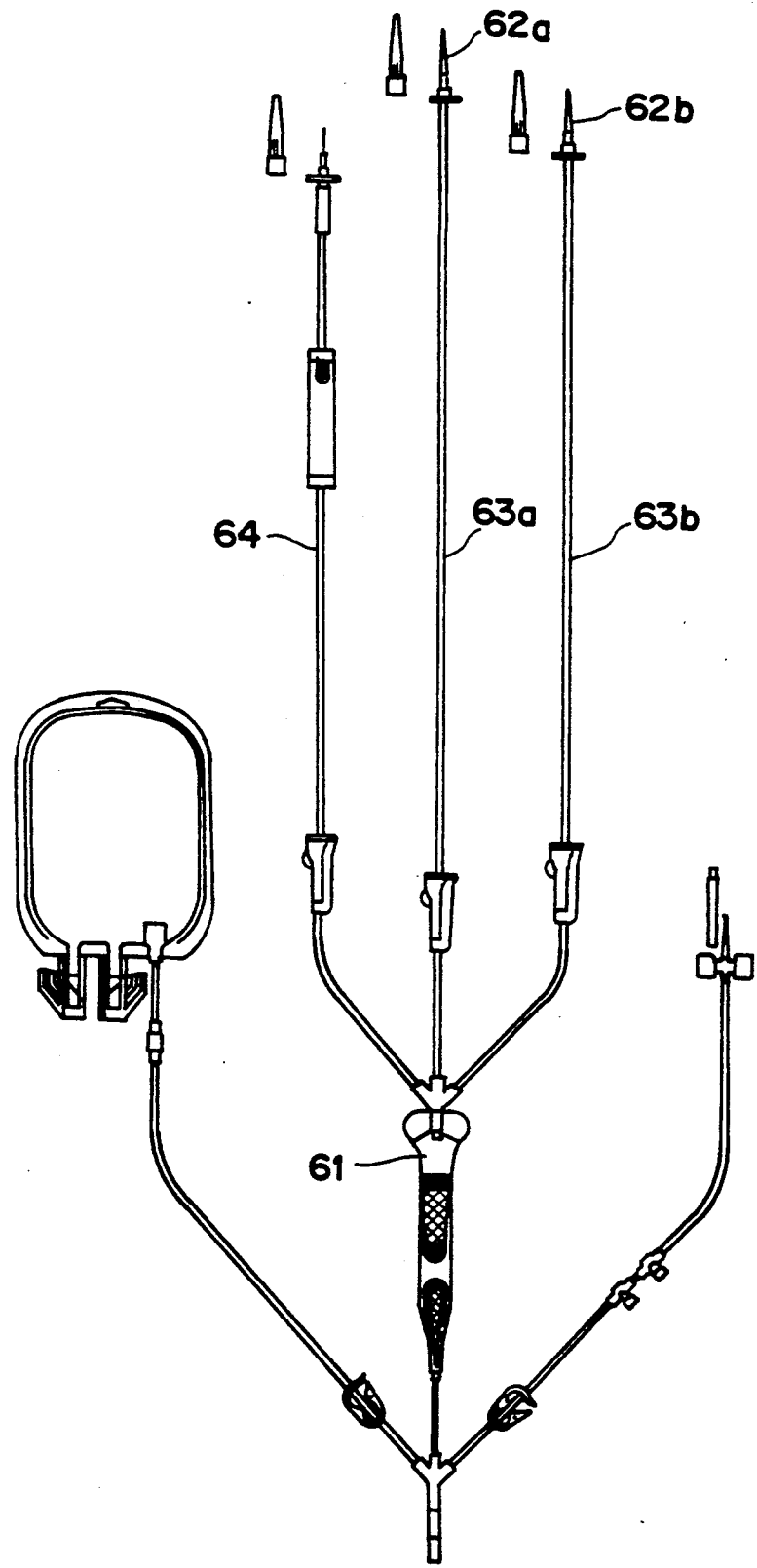
FIG. 5 (a) and 5(b) are schematic views showing other examples of a liquid transferring member and a blood transfusing member constituting a switch bag type blood-gathering set.

FIG. 1 is a schematic view showing one example of a switch bag type blood-gathering set of the present invention.

The switch bag type blood-gathering set 1 is basically constituted by a liquid transfer member 2, blood transfer members 3a and 3b, a blood-transfusing and blood-gathering member 4, blood storing members 5a and 5b, and a washing solution storing member 6.

The liquid transfer member 2 comprises a liquid introducing needle 7a which is provided a needle 7c made of a stainless, etc. to a needle base 7b, connecting tubes 8 and 9 made of a flexible polyvinyl chloride, etc., and an intravenous drip tube 11 made of a polyvinyl chloride, etc. loaded a filter 10 made of a polyamide such as Nylon (trade name), etc.

The blood transfusing member 3a is composed of an intravenous drip tube 12a made of a polyvinyl chloride, etc. and a connecting tube 13a made of a flexible polyvinyl chloride, and said intravenous drip tube 12a is loaded inside thereof filters 14a, 15a and 16a made of a polyethyleneterephthalate, etc. having different pore size, respectively. Also, at the ends of the intravenous drip tube 12a, the blood introducing needle 17a made of a polycarbonate, etc. and the connecting tube 18a (made of polyvinyl chloride, etc.) with the above connecting tube 13a.

The above blood-transfusing and blood-gathering member 4 comprises a blood-transfusing and blood-gathering needle 20a in which a needle 20b made of a stainless steel, etc. is provided into a needle base 20c and a rotary wing 20c is further provided to the needle base 20c, and connecting tubes 21 and 22 made of a flexible polyvinyl chloride, etc. Between these two connecting tubes 21 and 22, mixing portions 23a and 24a made of a polycarbonate, etc. buried puncture buttons 23b and 24b made of a silicone rubber, etc. are attached.

The washing solution storing member 6 is composed of a liquid discharging bag 26 made of a flexible polyvinyl chloride, etc. and connecting tubes 27 and 28 similarly made of a flexible polyvinyl chloride, etc. Each ends of said connecting tubes 27 and 28, male lure connectors 29 and 30 are provided as shown in FIG. 8, and both of the male lure connectors 29 and 30 are connected by a connecting tube 31 made of a silicone rubber, etc.

At a discharged liquid inlet 32 of the liquid discharging bag 26, a check valve 33 made of a flexible polyvinyl chloride or a silicone rubber, etc. is provided thereto.

The blood storing members 5a and 5b are composed of parent bags 35a and 35b, children bags 36a and 36b, and connecting tubes 37a, 37b, 38a and 38b, and connecting pieces 39a and 39b made of a polycarbonate, etc. are provided at inner portions of the above connecting tubes 37a and 37b. In these connecting pieces, a cylindrical body made of a hard resin and one end of which is encapsulated, and flow passages are sealed by the cylindrical bodies. When using it, one end terminated is broken whereby the flow passage is opened. Such connecting pieces have widely been utilized for blood transfusing site, etc. of the conventional blood-gathering bag.

In the above parent bags 35a and 35b, as an anticoagulant of the blood, solutions of
(1) CPD solution comprising citrate, phosphate and dextrose, and
(2) ACD solution comprising adenine, citrate and dextrose are charged.

These constituting members 2, 3a, 3b, 4, 5a, 5b and 6 are connected by connecting tubes 41, 42 and 43 made of a polyvinyl chloride through connecting tubes 9, 13a, 13b, 21, 22, 27, 28, 37a, 37b and 40, respectively.

To these connecting tubes 9, 13a and 13b, roll clamps A, B and C made of a polyethylene, etc. are provided.

To these connecting tubes 22, 27 and 40, clamps D, E and F made of a polypropylene, etc. are provided.

To these connecting tubes 37a and 37b, slide clamps G and H made of a polypropylene, etc. are provided.

The liquid introducing needle 7a, the blood introducing needle 17a and the blood-transfusing and blood-gathering needle 20a are sealed with needle caps 101, 102 and 103 made of a polypropylene, etc., respectively, so as to not contact with the air outside.

Next, the using method of the present invention will be explained by referring to FIG. 1.

(1) Priming operation

By closing the roll clamps A, B and C, and the clamps D, E and F, the liquid introducing needle 7a is connected to an apparatus (not shown in the figure) encapsulated with a physiological saline solution.

By opening the roll clamp A, the physiological saline solution is injected into an intravenous drip cylinder 11 to a predetermined liquid level with pumping the intravenous drip cylinder 11.

When reached to the predetermined liquid level, the roll clamp B is opened and the physiological saline solution is introduced into inside of an intravenous drip cylinder 12a throught the connecting tubes 9 and 13a. When reached to the predetermined liquid level, the roll clamp C is further opened and the physiological saline solution is also similarly introduced into the intravenous drip cylinder 12b with a predetermined liquid level.

Subsequently, clamps D, E and F are opened, physiological saline solutions are added dropwise while adjusting the opening degree of the roll clamp A in order to expel the air in the connecting tubes 40, 27 and 28 with the physiological saline solution into a discharged liquid bag 26 whereby priming is finished by closing the clamps D, E and F.

(2) Blood-gathering at the first time

By breaking the connecting piece 39a of the connecting tube 37a to open the flow passage, and after opening the slide clamp G, the blood-transfusing and blood-gathering needle 20a is punctured to a blood donor and the clamp E is opened.

The blood is supplied into a parent bag 35a through the blood-transfusing and blood-gathering needle 20a, and the connecting tubes 21, 22 and 37a.

After finishing collection of the predetermined amount of blood, closing the slide clamp G and opening the roll clamp A and the clamp D, the physiological saline solution is added dropwise from the liquid transferring member 2 into the blood-transfusing and blood-gathering member 4 through the connecting tube 40.

At this time, the blood-transfusing and blood-gathering needle 20a should be remained at the state of puncturing into the blood donor. This is to maintain the closed system after finishing the blood-gathering.

To do so, solidification due to accumulation of blood in the liquid transferring and blood-gathering member 4 during the transitional period to the next operation can be prevented.

(3) Blood-transfusing operation

A blood bag (not shown in the figure) in which blood is previously stored and contained therein by the prior blood-gathering is connected to the blood introducing needle 17a of the blood transfusing member 13a.

When the roll clamp A is opened and the roll clamp C is closed, the blood is transfused to a blood donor through the connecting tubes 13a, 40, 22 and 21 and the blood-transfusing and blood-gathering needle 20a. The blood transfusing rate at this time is preferably about 60 ml/min (the degree that an appearance running down to the center of instillation does not become a continuous line).

After finishing the transfusion of the blood in this blood bag, the roll clamp B is closed.

Then, the roll clamp A is opened again, the physiological saline solution is introduced into the blood-transfusing and blood-gathering member 4 in order to prevent solidification of the blood remained in the blood-transfusing and blood-gathering member 4.

(4) Blood-gathering at the second time.

By breaking the connecting piece 39b, the clamp H and the clamp E are opened.

The blood is introduced into the parent bag 35b through the blood-transfusing and blood-gathering needle 20a and the connecting tubes 21, 22 and 37b.

After gathering the predetermined amount of blood, closing the clamp E and opening the clamp A, the physiological saline solution is added dropwise from the liquid transferring member 2 to the blood-transfusing and gathering member 4.

(5) Termination

By closing the clamp E, an electrolyte previously prepared is supplemented to the blood donor through the mixing part 23a, the connecting tube 21 and the blood-transfusing and gathering needle 20a.

Finally, the connecting tubes 37a and 37b are sealed and welded by a welder, and then the blood storing members 5a and 5b are cut off to be use for the next blood transfusion by storing them at 4° C.

As the other examples of the switch bag type blood-gathering set of the present invention, numbers of the blood-transfusing member(s) and the blood storing member(s) may optionally be combined.

For example, embodiments of (1) two blood-transfusing members (3a and 3b) and three blood-storing members (5a, 5b and 5c) (see FIG. 2), (2) three blood-transfusing member (3a, 3b and 3c) and three blood-storing members (5a, 5b and 5c) (see FIG. 3), and (3) three blood-transfusing member (3a, 3b and 3c) and four blood-storing members (5a, 5b, 5c and 5d) (see FIG. 4) may be considered.

Further, by combining numbers of the blood storing member (5a to 5d) and volumes of the parent bags (38a, to 38d) in said blood storing member (5a to 5d), ten different embodiments can be carried out.

As shown in Table 1, an amount of blood to be reserved can be determined before blood-gathering by combining blood-gathering patterns in accordance with the condition of health and physical strength of the blood donor.

TABLE 1

|  | Initial | Second time | Third time | Fourth time | Fifth time | Blood amount reserved |
|---|---|---|---|---|---|---|
| Example 1 | 200 ml × 1 | 200 ml × 2 | 300 ml × 2 | 400 ml × 2 | 500 ml × 2 | 1000 ml |
| Example 2 | 300 ml × 1 | 300 ml × 2 | 300 ml × 3 | 400 ml × 3 | 500 ml × 3 | 1500 ml |
| Example 3 | 400 ml × 1 | 400 ml × 2 | 400 ml × 3 | 400 ml × 4 | 500 ml × 4 | 2000 ml |
| Example 4 | 200 ml × 2 | 200 ml × 2 | 200 ml × 2 |  |  | 800 ml |
| Example 5 | 200 ml × 2 | 200 ml × 2 | 200 ml × 3 |  |  | 1200 ml |

Remarks (1) Example 1 to Example 3 are examples of the method in which the blood gathered at the initial time is transfused at the next time and further blood is gathered excessively 200 ml to 400 ml, and these procesures are repeated.

(2) Example 4 and Example 5 are examples of the method in which blood-gathering of 200 ml×2 is carried out at the initial time, and at the second time, the third time, etc., 200 to 400 ml of excessive amount of blood is gathered and these procedures are repeated.

(3) As the other methods, according to the system of switch bagging every two weeks by dividing examples of Example 1 to Example 3 into two system, a large amount of blood may be reserved.

Also, in accordance with an amount of hemoglobin before blood-gathering of the blood donor may be reserved.

(4) While Example 1 to Example 5 are basic examples, by using this system, larger amount of blood can be reserved by increasing the number of times or combining Example 1 to Example 5.

Next, modified examples of each part of the switch bag type blood-gathering set of the present invention will be explained.

When the blood transfusing member is two pair or more, as shown in FIG. 5(a), plural numbers of the connecting tubes 63a and 63b in which the blood inlet needles 62a and 62b are provided may be fit to one intravenous drip cylinder 61. Or else, as shown in FIG. 5(b), the connecting tube 64 of the liquid transferring member may be provided to the intravenous drip cylinder with the aforesaid connecting tubes 63a and 63b.

By this constitution, numbers of parts just omitted intravenous drip cylinders can be reduced.

Concrete embodiments of the check valve 33 formed at the washing solution storing member 6 are shown in FIG. 6 and FIG. 7.

A check valve 64 of FIG. 6 is formed by laminating two sheets 65 made of a flexible polyvinyl chloride and heat sealing ends 66 thereof.

A check valve 67 of FIG. 7 is a generally so-called "duck's bill valve" and is integrally formed by a flexible polyvinyl chloride or a silicone rubber. Reference numeral 68 is a bill portion formed to a thin state.

By providing these check valves 64 and 67 to a waste solution inlet 32 of a waste liquid bag 26, when pressure is applied from outside of the waste liquid bag 26 after introducing a washing solution in the waste liquor bag 26, said external pressure functions to the direction of crushing the sheets 65 and 65 of the check valve 64 or the bill portion 68 of the check valve 67, whereby sanitariness can be retained without invading again the used washing solution into inside of the switch bag type blood-gathering set.

The male lure connectors 29 and 30 provided at the ends of the connecting tubes 27 and 28 of the washing solution storing member 6 can be used as shown below.

When the blood donor is punctured with the blood-transfusing and gathering needle 20a to carry out blood-gathering, if the trouble due to clogging of blood cells at inside of the needle 20b of the blood-transfusing and gathering needle 20a is caused, the connecting tube 31 is detached and the male lure connector 30 is exposed. Next, this male lure connector 30 is connected, for example, as shown in FIG. 9, to a female lure connector 72 of the blood-gathering needle 71 which is prepared for a spare and the blood donor is punctured with the blood-gathering needle 71.

The blood is introduced into the parent bag 35a of the blood storing member 5a through the connecting tubes 27 and 37a. To the contrary, the blood-transfusing and gathering needle 20a is employed for disposing waste liquor by connecting with the other male lure connector 29.

Pore sizes of filters 14a, 15a and 16a charged at inside of the intravenous drip cylinder 12a are formed as 210 μm, 160 μm and 35 μm, respectively, so as to become smaller from the inlet of the blood to the outlet direction. By this constitution, it can be completely prevented to invade microaggregates in the blood into the switch bag type blood-gathering set.

As the method fo attaching the filters 14a, 15a and 16a to inside of the intravenous drip cylinder 12, the following methods may be mentioned.

(1) 14a and 15a are laminated and welded in the intravenous drip cylinder, and 16a is welded and fit to the bottom end of the intravenous drip cylinder.

(2) 14a, 15a and 16a are laminated together, and welded and fit to inner surface fo the intravenous drip cylinder.

A child bag 36a in the blood storing member 5a (which is fit to the parent bag 35a through the connecting tube 38a) is employed when the blood gatheredd in the parent bag 35a is sampled to apply to the blood inspection, etc. It is particularly useful for the blood inspection which requires a large amount of a sample.

As stated above, since the blood-gathering is effected by repeating blood-gathering and blood-transfusion wherein the amount of gathered blood is relatively somewhat larger than the transfused blood and supplementation of the blood corresponding to the amount of the blood gathered from the blood donor is carried out to the blood donor, a burden charged to the blood donor is little.

Also, the numbers of liquid introducing needles 7a, blood introducing needles 17a and the blood-transfusing and gathering needle 20a or the shape of the connecting tubes 4, 42 and 43, and the materials of each constituting members 2, 3a, 4, 5a and 6 can optionally be determined depending upon purposes.

FIG. 10 is the other example of the present invention, and the difference from that of FIG. 1 is to connect connecting members 51a, 51b and 51c with the connecting tube 43 instead of connecting with the blood storing members 5a and 5b.

The connecting member 51a (51b and 51c are also the same) is composed of a connector member, i.e. a male connector 52a, and a connecting tube 55a, a lock nut 53a of said male connector 52a is freely fit. The male connector 52a and the lock nut 53a are sealed by a protector 54a so as to not be in contact with the air outside.

The connecting member 51a is constituted by a material such as a polyvinyl chloride, a polypropylene, a polycarbonate, etc.

These connecting members are connected with the connecting tube 42 through the connecting tube 43 made of a hard polyvinyl chloride, etc.

FIG. 11 is the aforesaid blood storing member 90 to be connected with the aforesaid connecting members 51a, 51b and 51c. Reference numeral 91 designates a parent bag made of a flexible polyvinyl chloride, etc., and similarly, 92 is a child bag, and they are connected with each other through a connecting tube 93.

In the above parent bag 91, the aforesaid blood anticoagulant containing the above components is charged.

At the top end of the above parent bag 91, connecting tubes 94 and 96 are joined and at the top end of the connecting tube 96, a female connector is provided. This female connector is constituted by a material such as a polyvinyl chloride, a polypropylene, a polycarbonate, etc. Also, at the midportions of the above connecting tubes 94 and 96, a connecting piece 95 made of a polycarbonate is fit, and to the connecting tube 96, the slide clamp G made of a polypropylene, etc. is fit.

A female connector 97a is sealed by a protector 98 so as to not be in contact with the air outside.

As the other examples of the above connecting members 5a, 5b and 5c, for example, as shown in FIG. 13, a female connector 111 (which is used as a blood transfusing inlet of the usual blood bag) inside of which is formed a thin film 110 is connected to a connecting tube 55a, and to a connecting tube 96 of the blood storing member 90, a needle member 112 may be provided. The needle member 112 is a plastic spike used in the conventional blood transfusing or liquid transferring set and it can break a thin film 110 when inserting it into the above female connector 111. The needle member 112 may be sealed with a needle cap in addition to a protector.

Next, using method of examples in FIG. 10 and FIG. 11 will be explained.

(1) Priming operation

The same as the aforesaid priming operation in FIG. 1.

(2) Blood-gathering at the first time

By breaking protectors 54a and 98, a male connector 52a of a connecting member 51a and a female connector 97 of a blood storing member 90 are connected with each other. At this time, in order to connect both connectors more fixedly, the connecting portion is tightened with a lock nut 53a.

By opening a connection piece 95 provided at the midportion of a connecting tube 94 to open blood flow passage of the connecting tubes 55a and 94, and puncturing the blood donor with a blood-transfusing and gathering needle 20a, a clamp E and a clamp G are opened.

By this constitution, the blood is introduced into a parent bag 91 through connecting tubes 21, 22, 55a, 96 and 94.

After completion of a predetermined amount of blood-gathering, the slide clamp G which is provided at the midportion of the connecting tube 96 is closed.

Thereafter, in the same manner as in the example of FIG. 1, a physiological saline solution is added dropwise into the blood-transfusing and gathering member 4.

(3) Blood transfusing operation

The same as in the operation of FIG. 1.

(4) Blood-gathering at the second time

New blood storing member 99 is prepared (which is other blood storing member than the blood storing member used in the blood-gathering at the first time).

Similarly as in the blood-gathering at the first time, blood is introduced from a blood donor into a new blood storing member.

After gathering a predetermined amount of blood, the clamp E is closed and a clamp A is opened, and a physiological saline solution is added dropwise from a liquid transferring member 2 into a blood-transfusing and gathering member 4.

(5) Termination

Similarly as in the operation in the example of FIG. 1, an electrolyte is supplemented to the blood donor.

Finally, the connecting tube 96 is sealed and welded by a welder, and then the blood storing member 90 is cut off to use for the next blood transfusion by storing it at 4° C.

As the modified example of FIG. 10, as shown in FIG. 12, by newly adding connecting tubes 44 and 45, a blood transfusing member 3c and connecting members 51d and 51e can be increased. As the protector, other than the embodiment shown in FIG. 1, the protector used in a blood transfusion inle of the conventional blood bag may be used.

FIG. 14 is a perspective view showing the summary of the switch bag type blood-gathering set shown in FIG. 4.

An operating panel 200 is basically constituted by a stand member 202, a body 203 and a mobile member 204.

FIG. 15 is a perspective view of the body 203 and the mobile member 204, FIG. 16 is a side view of FIG. 15, and FIG. 17 is a schematic view of the stand member 202.

The stand member 202 is composed of a hanger 206 provided with a plural number of hooks 205, a lod-shaped prop 207, and a backboard having an angular shape, and the hanger 206 is provided at the top end of the prop 207 and the backboard 206 is attached to the midportion of the prop 207.

The body 203 is basically constituted by a ceiling board 209, a side board 210 and a bottom board 211. The ceiling board 209 and the bottom board 211 are formed so as to be opposite to each other through the side boards 210.

To the aforesaid ceiling board 209, a pull 212 and an inserting hole 213 of the prop 207 of the aforesaid stand member 202 are formed.

At the top end of the aforesaid bottom board 211, a curtain board 214 projects. Inside of the body 203 is made hollow (hereinafter referred to "space 217").

The mobile member 204 is composed of a bottom board 215 and wheels 220, and the wheels are provided at the back of the bottom board 215. The aforesaid body 203 and the mobile member 204 are attached via a leg 216. The top end of the leg 216 is fixed to the back of the ceiling board 209 and to rear end portion of the bottom board 211. Inside of the leg 216 is made hollow (hereinafter referred to "space 218"), and at the upper side portion of the leg 216, a fixing member 219 of the prop 207 is attached. The prop 207 is inserted into the space 218 of the leg 216 through the inserting hole 213 formed at the rear of the ceiling board 209, and up and down movement of the prop 207 is controlled by the fixing member 219. At the aforesaid backboard 208, fixing members 211 to 216 which are to fix the connecting tubes 8 and 9 connecting the liquid transferring member of the above switch bag type blood-gathering set, the blood transfusing members 3a to 3c and a supplmenting liquid member (mentioned hereinbelow); and connecting tubes 13a to 13c of the intravenous drip cylinder 13a to 13c are provided.

FIG. 18 shows details of the above backboard 8. Reference numerals 221a to 226a are fixed grooves of the connecting tubes of the above blood-gathering bag, and reference numerals 221b to 226b are screws for fixing said fixing members 221 to 226 to the backboard of the operating panel 201.

To the aforesaid backboard 208, colored line markers 279, 280, 282 and 283a to 283c are attached as signs of the positions to fit each of the above various connecting tubes 8, 9 and 13a to 13c.

To the connecting tube 9 of the liquid transferring member 2, the marker 279 (green) corresponds and to the connecting tubes 13a to 13c of the blood-transfusing members 3a to 3c, the markers 283a to 283c (red) correspond. The marker 282 (blue) corresponds to the connecting tube of the supplementing liquid member. The marker 280 (red) corresonds to the connecting tube 40.

FIG. 19 shows details of the ceiling board 209. Reference numerals 227a to 233a designates fixed grooves of the connecting tubes, and reference numerals 227b to 233b designates screws for fixing the fixing members 227 to 233 to the above ceiling board 209.

To the ceiling board 209, each of connecting tubes 22, 27, 37a to 37d of a blood-transfusing and gathering member 4, blood storing members 5a to 5d and a washing solution storing member 6, as well as fixing members 227 to 233 for fit and fix mixing injection portions 23a and 23b are provided.

Also, to the ceiling board 209, colored line markers 281, 290, 291 and 287a to 287c are attached as signs of the positions to fit each of the above various connecting tubes 22, 27 and 37a to 37d.

To the connecting tube 22 of the blood-transfusing and gathering member 4, the marker 291 (red) corresponds, and to the connecting tubes 37a to 37d of the blood storing members 5a to 5d, the markers 287a to 287d (red) correspond. The marker 290 (black) corresponds to the connecting tube 27 of the washing solution storing member 6.

The above backboard 208 is as shown in FIG. 20 (which is, rear view of FIG. 14 and an, enlarged view in the vicinity of the backboard 208) connected to a prop 207 with metal fittings 270 formed with an U-shaped groove 269, and can be controled to move up and down by tightening with a fixing member 271.

Next, details of the fixing members 221 to 226 and 227 to 233 will be explained.

FIG. 21 is the first embodiment of the fixing member.

At the surface of the fixing member 241, a groove 243 for fixing a connecting tube is formed, and at the top edge of the fixing groove 243, a notch 242 is formed. The width W of the notch 242 is formed slightly smaller than an outer diameter of the connecting tube so as to not easily leave the connecting tube.

At the rear of the fixing member 241, a screw hole 244 is formed to the direction intersecting to the length direction of the fixing groove 243 of the connecting tube.

The fixing member 241 is as shown in FIG. 22, fixed to the backboard 208 (the ceiling board 209 is also the same). When the fixing member 241 is attached to the backboard 208, by overlapping the screw hole 244 with the position of a screw hole 245 formed at the backboard 208 and inserting a screw 246 from the rear face of the backboard 208 into the screw holes 244 and 245 to fix the fixing member 241.

Various connecting tubes constituting the switch bag type blood-gathering set are put in the fixing groove 243 of the fixing member 241 with pressure.

FIG. 23 is a second embodiment of the fixing member.

At the front surface of the fixing member 251, a groove 253 for fixing a connecting tube and a mixing portion is formed, and at the upper edge of the fixing groove 253, a notch 252 is formed. The width W' of the notch 252 is formed slightly smaller than the outer diameter D' of the connecting tube so as to not easily leave therefrom the connecting tube and the mixing portion fixed to said fixing groove 253.

At the rear surface of the fixing member 251, a screw hole 254 is formed to the direction which is the same with the length direction of the fixing groove of the connecting tube and the mixing portion.

FIG. 24 shows a schematic view in which a switch bag type blood-gathering set is fixed by using the above fixing members 241 and 251 (wherein the fixing member 241 is mainly used for fixing the connecting tube and the fixing member 251 is mainly used for fixing the mixing portion).

Next, a method of using the above operating panel will be explained by referring to FIG. 4.

(1) Attachment of the switch bag type blood-gathering set 1 to the operating panel 200

Each constituting member which constitutes the switch bag type blood-gathering set is attached to the operating panel as shown below.

Connecting tubes 8, 9 and 13a to 13c constituting the liquid transferring member 2 and the blood transfusing members 3a to 3c are fixed to fixing members 221 to 226.

Connecting tubes 22, 27 and 37a to 37d which connect a blood-transfusing and gathering member 4 and blood storing members 5a to 5d with a washing solution storing member 6, and mixing portions 23a and 23b are fixed to the fixing members 227 to 233 of the ceiling board 209.

The blood storing member 5a is placed on a blood-gathering scale 350, and the blood storing members 5b to 5d and the washing solution storing member 6 are placed on a bottom borad 211 of the operating panel 200.

(2) Priming operation

An apparatus 351 charged with physiological saline solution is attached to a hook 205.

Next, closing roll clamps A, B, C and D as well as clamps D, E and F, and a liquid introducing needle 7a is connected to the above apparatus 351.

Subsequently, in the same manner as in the priming operation of the example of FIG. 1, priming in the switch bag type blood-gathering set is carried out.

(3) Blood-gathering at the first time

In the same manner as in the example of FIG. 1, a predetermined amount of blood is gathered through the blood-transfusing and gathering needle 20a to a blood storing member 5a. This blood storing member 5a is contained in a body 203, while a blood storing member 5b is taken out from the bottom board and placed on the blood gathering scale 305.

The following procedures are the same as with the example of FIG. 1.

(4) Blood transfusing operation

A previously gathered and reserved blood bag 325 is attached to a hook 205, and a liquid transferring member 13a is connected to the blood bag 325. Thereafter, the blood in the blood bag is transfused to the blood donor through the blood-transfusing and gathering needle 20a.

Other operations are the same as with the transfusing operation of FIG. 1.

(5) Blood-gathering at the second time

In the same manner as in the example of FIG. 1, the blood is introduced from the blood-transfusing and gathering needle 20a to a parent bag of the blood storing member 5b. Thereafter, blood-transfusion and blood-gathering operations are successively repeated.

(6) Termination

Finally, the clamp E is closed, according to the supplementing liquid member 345 previously prepared, a supplementing solution of an electrolyte is injected to the blood donor. This supplementing liquid member 345 is constituted by an apparatus 355 in which an electrolyte is charged therein, other connecting tubes 346 and 348, an intravenous drip cylinder 347 and a liquid transfusing needle 349. The above apparatus 355 is fit to a hook 205 whereby the connecting tube 346 is fixed to the fixing member 225. The liquid transferring needle 349 is connected to the mixing portion 23a whereby the electrolyte is supplemented to the blood donor through the mixing portion 23a, the connecting tube 21 and a blood-transfusing and gathering needle 20a. Finally, the connecting tubes 37a and 37b are sealed and welded by a welder, and the blood storing members 5a and 5b are cut off therefrom to be used for the next blood transfusion by storing them at 4° C.

The operating panel is not limited to those having the shape of FIG. 14, and the backboard may be formed integrally with and vertically to the ceiling board.

The number of the markers is not limited to those shown in FIG. 18 and FIG. 19, but it may be attached depending upon the number of the connecting tubes of the switch bag type blood-gathering set fixed to the operating panel 1.

Coloring of the marker is not limited to the aforesaid embodiments, but it may anyone so long as it can clearly confirm the flow passage of the blood and other liquids at liquid transferring, blood-transfusing and blood-gathering. Color such as yellow, purple, white, etc. may be optionally used in combination.

Shape of the marker is not limited to the line-shape, but it may be a groove shape. That is, a groove is formed on the surface of the backboard or the ceiling board, and a connecting tube of the switch bag type blood-gathering set is fit and fixed, and it may be fixed thereon with a fixing member so as to not detach the connecting tube from the groove.

If the above operating panel is used, plural and various connecting tubes do not interlock with each other since arrangement of each constituting member constituting the switch bag type blood-gathering set and the connecting tubes connecting these members can be fixed in good order. Also, since flow passages of the blood and other liquids at liquid transferring, blood-transfusing and blood-gathering can be grasped at a galnce, operation can be easily carried out and there is no fear of occurring an accident due to mishandling.

As the switch bag type blood-gathering set to be used for a technique for predeposit of autologus blood, in addition to the aforesaid examples, a switch bag type blood-gathering set as shown in FIG. 25 can be used.

This blood-gathering set is a modified example of the switch bag type blood-gathering set shown in the above FIG. 4. Difference from FIG. 4 consists in omission of the liquid transferring member 2, the washing solution storing member and each children bags of the blood storing members 5a, 5b, 5c and 5d. Other constitution is the same with that of FIG. 4.

Capacity and number of the blood transfusing members 3 and the blood storing members 5 may optionally be selected.

Next, an application example of the switch bag type blood-gathering set shown in FIG. 25 will be explained as follows.

First application example

At the first time, one unit of a blood A is gathered in a blood storing bag 400 (see FIG. 26(a)).

At the second time as shown with an arrow in FIG. 26(b), (1) one unit of a blood B is gathered through a blood-transfusing and gathering member 4 via a connecting tube 37a into a blood storing bag 2a, (2) the blood A gathered at the first time is transfused to the patient through a blood transfusing member 3 and the blood-transfusing and gathering member 4, and (3) in the same manner as in (1), a blood B is gathered from the patient through the blood-transfusing and gathering member 4 and an inlet tube 37b into a blood storing bag 402b, whereby the blood B in excess of one unit than that of the first time is gathered.

At the third time as in the second time as shown with an arrow in FIG. 26(c), (1) one unit of a blood C is gathered from the patient into a blood storing bag 402c, (2) one unit of the blood B is transfused to the patient from the blood storing bag 402a, (3) one unit of a blood C is gathered from the patient into a blood storing bag 402a, (4) one unit of the blood B is transfused to the patient from the blood storing bag 402b, and (5) one unit of a blood C is gathered from the patient into a blood storing bag 402e.

At the fourth time as in the above as shown with an arrow in FIG. 26(d), (1) one unit of a blood D is gathered from the patient into a blood storing bag 402f, (2) one unit of the blood C is transfused to the patient from the blood storing bag 402c, (3) one unit of a blood D is gathered from the patient into a blood storing bag 402g, (4) one unit of the blood C is transfused to the patient from the blood storing bag 402d, (5) one unit of a blood D is gathered from the patient into a blood storing bag 402h, (6) one unit of the blood C is transfused to the patient the blood storing bag 402e, and (7) one unit of a blood D is gathered from the patient into a blood storing bag 402i.

However, each blood-gathering should be carried out with the interval of within the effective preservation term of the blood (within 21 days from blood-gathering).

As described above, the present application example is the technique for predeposit of autologus blood in which n units of bloods gathered from the first time to the Nth time are transfused to the patient at the (N+1)th time and at the same time, (n+1) units of bloods are gathered.

By the operation as mentioned above, the patient is always wherein only in excess of one unit of blood, and the blood gathered at the Nth time is certainly transfused to the patient at the (N+1)th time so that a large amount of fresh bloods can be always deposited.

Second application example

In the same manner as in the first application example, each one unit of bloods A and B is gathered in blood storing bags 400a and 400b at the first and the second times, respectively (see FIG. 27(a) and (b)).

At the third time, as shown with an arrow in FIG. 27(c), (1) one unit of a blood C is gathered from a patient through a blood-transfusing and gathering member 4 via an inlet tube 37a into a blood storing bag 402a, (2) one unit of the blood A gathered at the first time is transfused to the patient through a blood transfusing member 3 and the blood-transfusing and gathering member 4, and (3) a blood C is gathered from the patient into a blood storing bag 402b, At the fourth time as in the third time as shown with an arrow in FIG. 27(d), (1) one unit of a blood D is gathered from the patient into a blood storing bag 402c, (2) one unit of the blood B gathered at the second time is transfused to the patient, and (3) one unit of a blood D is gathered from the patient into a blood storing bag 402d.

At the fourth time as shown with an arrow in FIG. 26(c), (1) one unit of the blood D is gathered from the patient into a blood storing bag 402c, (2) one unit of the blood B gathered at the second time is transfused to the patient, and (3) one unit of a blood D is gathered from the patient into a blood storing bag 402d.

At the fifth time as shown with an arrow in FIG. 26(c), three units of bloods D are gathered from the patient as well as two units of bloods 402c gathered at the fourth step are transfused, and the procedures are carried out alternately.

As described above, the present application example is a technique for predeposit of autologus blood in which n units of bloods gathered at the Nth time are transfused to the patient at the (N+2)th time as well as (n+1) units of bloods are gathered from the patient and stored, and said bloods are transfused to the patient at the [(N+2)+2]th time.

Thus, in the second application example, since the first application example is divided into two series and blood-gathering is carried out, as compared with the first application example, number of the blood storing bag(s) used at the time carrying each operation does not change so that the time spent to work can be shortened and a large amount of predeposit of blood can be realized.

However, the blood-gathering time of each one series such as the first time and the third time, etc., it should be carried out within interval during effective preservation term of blood (within 21 days from blood-gathering).

Third application example

As shown in FIG. 28(a) to (c), each one unit of bloods A, B and C (total three units of bloods) are gathered in blood storing bags 400a, 400b and 400c, respectively, at the first to the third times, and at the fourth time, as shown with an arrow in FIG. 28(d), (1) one unit of a blood D is gathered from the patient into a blood storing bag 402a, (2) one unit of the blood A gathered at the first time is transfused to the patient, (3) one unit of a blood D is gathered from the patient into a blood storing bag 402b, (4) one unit of the blood B gathered at the second time is transfused to the patient, (5) one unit of a blood D is gathered from the patient into a blood storing bag 402c, (6) one unit of the blood C gathered at the third time is transfused to the patient, and (7) one unit of a blood D is gathered from the patient into a blood storing bag 402d.

As described above, the present application example is a technique for predeposit of autologus blood in which n units of bloods gathered at from the first time to the Nth time are transfused to the patient at the (N+1)th time as well as (n+1) units of bloods are gathered from the patient.

Thus, the whole amounts of bloods gathered at the last time are returned to the patient and bloods in excees of one unit are newly gathered from the patent (intervals from the first blood-gathering to the final time should be within 21 days which are effective preservation term of bloods).

By using this method, fresh blood can relatively easily be stored within the limited range.

In the blood storing bags (400, 400a to 400c and 402a to 402i) shown in the above FIG. 26 to FIG. 28, an anticoagulant of blood having the composition as mentioned above is charged.

As described above, the present invention is an excellent invention having the effects of (1) since blood gathered from the blood donor can be transfused without losing freshness as well as larger amounts of bloods than those transfused to the donor can be gathered from the donor without preventing balance of body fluid, and they can be used with a recycle system, it is the most suitable for autologus blood of the donor, (2) since each of constituting members is integrally connected whereby operation can be carried out with a closed system and thus sanitation can be secured, (3) a certain amount (100 to 500 ml) of blood can be gathered with one blood-gathering operation and hepatic function is normal with the degree of metabolizing citric acid in the stored blood, and also it is efffective for an operation of a patient who has not trouble drived from blood (such as orthopaedic operation), and (4) it is also effective in the case where a patient has a rare blood type and it can be judged that a sufficient amount of blood cannot be secured for operation.

What is claimed is:

1. A blood-gathering set of a switch-bag type for performing blood transfusion of blood gathered from a blood donor and stored beforehand to the same blood donor, and storing blood afresh by performing blood gathering afresh from the blood donor, said blood-gathering set comprising:

liquid transfer means including a liquid introducing needle connectable to a container in which a medicament solution such as physiological salt solution or the like is stored, a first connecting tube connected to the liquid introducing needle, and a drip cylinder connected to the first connecting tube at a midpoint of the first connecting tube;

blood-transfusing means including N individual (N≧2) blood-introducing needles connectable to blood bag means in which blood from the blood donor is stored to introduce blood contained in the blood bag means to the donor during subsequent transfusion, drip cylinder means connected with the blood introducing needles and provided with filter means inside thereof, and a second connecting tube connected with the drip cylinder means;

blood-transfusing and blood-gathering means including a gathering needle for performing one of blood transfusion of blood introduced by said blood transfusion means to the blood donor and blood-gathering from the same blood donor, a third connecting tube connected to the gathering needle for guiding blood, and a medicament solution introducing portion connected to the third connecting tube at a midportion of the third connecting tube;

washing solution storing means including a waste liquor bag for recovering waste liquor after priming of the blood-gathering set, a fourth connecting tube for guiding waste liquor to an inside of the waste liquor bag, and a valve arranged in the inside of the waste liquor bag for preventing countercurrent;

n individual blood-storing members (n≧2 and n≧N) each including a blood-gathering bag for storing blood, a fifth connecting tube for communicating said blood-transfusing means and blood-transfusing and blood-gathering means with the blood-gathering bag, the fifth connecting tube having a connecting piece with flow channel which is open when the set is in use, and a second bag connected with the blood-gathering bag; and a plurality of joining members associated with the liquid transfer means, blood-transfusing means, and blood-transfusing and blood-transfering means for preventing invasion of outside air therein.

2. A blood-gathering set according to claim 1, comprising a connector connected with said first and second connecting tubes, connecting means for communicating the connector and the third, fourth, and fifth tubes with each other, and a sixth tube for connecting the connector with the connecting means.

3. A blood-gathering set according to claim 2, wherein each of said third, fourth, fifth, and sixth connecting tubes is provided with clamping means.

4. A blood-gathering set according to claim 1, wherein the washing solution storing means includes an element for connecting the waste liquor bag with the fourth connecting tube.

5. A blood-gathering set according to claim 2, further comprising n connector elements for removably connecting the individual blood-storing members with the connecting means.

6. A blood-gathering set according to claim 1, wherein the blood-transfusing means includes N individual (N≧2) blood-transfusing members each including a blood-introducing needle, the drip cylinder means including N individual drip cylinders connected with respective blood-introducing needles, and N second connecting tubes connected with the separate drip cylinders, respectively.

* * * * *